(12) United States Patent
Barden et al.

(10) Patent No.: US 8,440,186 B2
(45) Date of Patent: May 14, 2013

(54) P2X7 EPITOPES

(75) Inventors: Julian Alexander Barden, North Ryde (AU); Angus Gidley-Baird, North Ryde (AU)

(73) Assignee: Biosceptre International Limited, North Ryde, NSW (AU)

( * ) Notice: Subject to any disclaimer, the term of this patent is extended or adjusted under 35 U.S.C. 154(b) by 169 days.

(21) Appl. No.: 12/677,799

(22) PCT Filed: Sep. 12, 2008

(86) PCT No.: PCT/AU2008/001364
§ 371 (c)(1),
(2), (4) Date: Jul. 1, 2010

(87) PCT Pub. No.: WO2009/033233
PCT Pub. Date: Mar. 19, 2009

(65) Prior Publication Data
US 2011/0177080 A1 Jul. 21, 2011

(30) Foreign Application Priority Data
Sep. 14, 2007 (AU) .............................. 2007905018

(51) Int. Cl.
*C07K 16/30* (2006.01)
*A61K 39/395* (2006.01)

(52) U.S. Cl.
USPC ............. 424/130.1; 424/133.1; 424/139.1; 424/141.1; 424/143.1; 530/387.1; 530/387.3; 530/387.9; 530/388.22

(58) Field of Classification Search .................. None
See application file for complete search history.

(56) References Cited

U.S. PATENT DOCUMENTS

| | | | |
|---|---|---|---|
| 6,133,434 A | 10/2000 | Buell et al. |
| 6,303,338 B1 | 10/2001 | Ni et al. |
| 6,306,393 B1 | 10/2001 | Goldenberg |
| 6,329,503 B1 | 12/2001 | Afar et al. |
| 6,709,832 B1 | 3/2004 | Von Knebel Doeberitz |
| 7,183,064 B1 | 2/2007 | Slater et al. |
| 7,326,415 B2 | 2/2008 | Barden et al. |
| 7,531,171 B2 | 5/2009 | Barden et al. |
| 7,767,789 B2 | 8/2010 | Gorodeski et al. |
| 7,888,473 B2 | 2/2011 | Barden et al. |
| 8,067,550 B2 | 11/2011 | Barden et al. |
| 8,080,635 B2 | 12/2011 | Barden et al. |
| 8,293,491 B2 | 10/2012 | Gidley-Baird et al. |
| 2004/0067542 A1 | 4/2004 | Barden et al. |
| 2007/0020706 A1 | 1/2007 | Gorodeski et al. |
| 2007/0248963 A1 | 10/2007 | Slater et al. |
| 2008/0131438 A1 | 6/2008 | Barden et al. |
| 2008/0227122 A1 | 9/2008 | Barden et al. |
| 2010/0036101 A1 | 2/2010 | Gidley-Baird et al. |
| 2011/0110959 A1 | 5/2011 | Barden et al. |
| 2011/0111431 A1 | 5/2011 | Slater et al. |
| 2012/0059151 A1 | 3/2012 | Barden et al. |
| 2012/0282278 A1 | 11/2012 | Barden et al. |

FOREIGN PATENT DOCUMENTS

| | | |
|---|---|---|
| AU | 64184/98 B2 | 10/1998 |
| CA | 2284859 C | 1/2007 |
| EP | 1006186 A1 | 10/1998 |
| WO | WO 92/16558 A1 | 10/1992 |
| WO | WO 95/33048 A2 | 12/1995 |
| WO | WO 97/06256 A2 | 2/1997 |
| WO | WO 97/41222 A1 | 11/1997 |
| WO | WO 98/42835 A1 | 10/1998 |
| WO | WO 00/50458 A1 | 8/2000 |
| WO | WO 01/06259 A1 | 1/2001 |
| WO | WO 01/30964 A2 | 5/2001 |
| WO | WO 02/48395 A1 | 6/2002 |
| WO | WO 02/057306 A1 | 7/2002 |
| WO | WO 03/020762 A1 | 3/2003 |
| WO | WO 2004/092384 A2 | 10/2004 |
| WO | WO 2007/027957 A2 | 3/2007 |
| WO | WO 2008/043145 A1 | 4/2008 |
| WO | WO 2008/043146 A1 | 4/2008 |
| WO | WO 2009/033233 A1 | 3/2009 |
| WO | WO 2009/033234 A1 | 3/2009 |
| WO | WO 2011/020155 A1 | 2/2011 |
| WO | WO 2011/075789 A1 | 6/2011 |

OTHER PUBLICATIONS

Buell et al. (1998). Blockade of human P2X7 receptor function with a monoclonal antibody. Blood. 92:3521-3528.*

Barden, J.A., et al., "Specific detection of non-functional human $P2X_7$ receptors in HEK293 cells and B-lymphocytes," *FEBS Letters*, vol. 538, pp. 159-162 (2003).

Gu, B., et al., "An $Arg^{307}$ to Gln Polymorphism within the ATP-binding Site Causes Loss of Function of the Human $P2X_7$ Receptor," *The Journal of Biological Chemistry*, vol. 279(30), pp. 31287-31295 (2004).

Wiley, J., et al., "An Ile-568 to Asn Polymorphism Prevents Normal Trafficking and Function of the Human $P2X_7$ Receptor," *The Journal of Biological Chemistry*, vol. 278(19), pp. 17108-17113 (2003).

Worthington, R.A., et al., "Point mutations confer loss of ATP-induced human $P2X_7$ receptor function," *FEBS Letters*, vol. 512, pp. 43-46 (2002).

U.S. Appl. No. 13/518,382, filed Jun. 21, 2012, Barden et al.
U.S. Appl. No. 60/686,770, filed Jun. 2, 2005, Gorodeski et al.

(Continued)

*Primary Examiner* — Christine J Saoud
*Assistant Examiner* — Jon M Lockard
(74) *Attorney, Agent, or Firm* — Alston & Bird LLP

(57) ABSTRACT

The invention relates to purinergic (P2X) receptors, more specifically to P2X7 receptors, the generation of antibodies and the use of antibodies and immunogens that are capable of selectively binding to a non ATP-binding P2X7 receptor but not to an ATP-binding P2X7 receptor, for the detection and treatment of disease conditions, especially cancer.

13 Claims, 6 Drawing Sheets

OTHER PUBLICATIONS

U.S. Appl. No. 60/778,993, filed Mar. 3, 2006, Gorodeski et al.
Ayyanathan et al., "Cloning and chromosomal localisation of the human P2Y1 purinoceptor," Biochem Biophys Res Commun, 218(3):783-788, (1996).
Bird et al., "Single-Chain Antigen-Binding Proteins," Science, 242(4877):423-426, (1988).
Bowler et al., "Identification and cloning of human P2U purinoceptor present in osteoclastoma, bone, and osteoblasts," J Bone Min Res, 10(7):1137-1145, (1995).
Buell et al., "P2X receptors: am emerging channel family," Eur J Neurosci., 8:2221-2228, (1996).
Burnstock et al., "P2 Purinergic Receptors: Modulation of Cell Function and Therapeutic Potential," J Pharm Exp Therap, 295:862-869, (2000).
Chan et al., "Localization of P2X1 purinoceptors by autoradiography and immunohistochemistry in rat kidneys," Am J Physiol Renal Physiol, 274(4(2)): F799-804, (1998).
Cheewatrakoolpong et al., "Identification and characterization of splice variants of the human P2X7 ATP channel," Biochem Biophys Res Comm., 332:17-27, (2005).
Chessell et al., "Dynamics of P2X7 receptor pore dilation: pharmacological and functional consequences," Drug Dev Res, 53(2-3):60-65, (2001).
Communi et al., "Cloning and Functional Expression of a Human Uridine Nucleotide Receptor," J Biol Chem, 270(52): 30849-30852, (1995).
Communi et al., "Cloning, Functional Expression and Tissue Distribution of the Human P2Y6 Receptor," Biochem Biophys Res Commun, 222:303-308, (1996).
Dangl et al., "Rapid Isolation of Cloned Isotype Switch Variants Using Fluorescence Activated Cell Sorting," Cytometry, 2:395—401, (1982).
DeRisi et al., "Exploring the Metabolic and Genetic Control of Gene Expression on a Genomic Scale," Science, 278: 680-686, (1997).
Di Virgilio et al., "Responses of mouse lymphocytes to extracellular adenosine 5'triphosphaste (ATP)," J Immunol 143:1955-1960, (1989).
Di Virgiolio et al., "Purinergic P2X7 receptor: a pivotal role in inflammation and immunomodulation," Drug Dev Res, 45:207-213, (1998).
Dixon et al., "Extracellular nucleotides stimulate proliferation in MCF-7 breast cancer cells via P2-purinoceptors," Br J Cancer, 75(1):34-39, (1997).
Dubyak et al., "Signal transduction via P2-purinergic receptors for extracellular ATP and other nucleotides," Am. J Physiol 265:C577-C606,(1993).
European Search Report of Sep. 18, 2008 for application EP08156593 (published as EP1961767).
Feng et al., "A truncated P2X7 receptor variant (P2X7-j) endogenously expressed in cervical cancer cells antagonizes the full-length P2X7 receptor through hetero-oligomerization," J Biol Chem, 281:17228-17237, (2006).
Feng et al., "ATP stimulates GRK-3 phosphorylation and 3-arrestin-2-dependent internalization of P2X7 receptor," Am J Physiol Cell Physiol, 288:C1342—C1356, (2005).
Feng et al., "Endogenously Expressed Truncated P2X, Receptor Lacking the C-Terminal (P2X7-RTr) is Preferentially Upregulated in Epithelial Cancer Cells and Fails to Mediate Ligand-Induced Pore Formation and Apoptosis," 10th Symposium European Society for (2005).
Feng et al., "Endogenously Expressed Truncated P2X7 Receptor Lacking the C-Terminus is Preferentially Upregulated in Epithelial Cancer Cells and Fails to Mediate Ligand-Induced Pore Formation and Apoptosis," Nucleosides, Nucleotides and Nucleic Acides, 25:1271-76 (2006).
Ferrari et al., "P2Z purinoreceptor ligation induces activation of caspases with distinct roles in apoptotic and necrotic alterations of cell death," FEBS Lett., 447:71-75, (1999).
Ferrari et al., "ATP-mediated cytoxicity in microglial cells," Neuropharmacology, 36 (9):1295-1301, (1997).

Foster et al., "Cellular and molecular pathology of prostate cancer precursors," Scand J Urol Nephrol Suppl.,34(205):19-43, (2000).
Galfre et al., "Antibodies to major histocompatability antigens produced by hybrid cell lines," Nature, 266:550-552, (1977).
Galfre et al., "Rat x rat hybrid myelomas and a monoclonal anti-Fd portion of mouse IgG," Nature, 277:131-133, (1979).
Gefter et al., "A simple method for polyethylene glycol-promoted hybridization of mouse myeloma cells," Somatic Cell Genet., 3(2):231, (1977).
GenBank: Accession No. Y09561, versions Y09561.1, "H. sapiens mRNA for P2X7 receptor". [Retrieved from the Internet May 24, 2011: <URL: http://www.ncbi.nlm.nih.gov/nuccore/y09561 >].
Georgiou et al., "Human Epidermal and Monocyte-Derived Langerhans Cells Express Functional P2X7 Receptors," J Invest Dermatology,125:482-490, (2005).
Giusti et al., "Somatic diversification of S107 from an antiphosphocholine to an anti-DNA autoantibody is due to a single base change in its heavy chain variable region," PNAS, 84:2926-2930, (1987).
Greenbaum et al., "Comparing protein abundance and mRNA expression levels on a genomic scale," Genome Biology, 4(9):117.1-117.8, (2003).
Greig et al., "Expression of Purinergic Receptors in Non-melanoma Skin Cancers and Their Functional Roles in A431 Cells," J Invest Dermatol, 121:315-327, (2003).
Groschel-Stewart et al., "Localisation of P2X5 and P2X7 receptors by immunohistochemistry in rat stratified squamous epithelia," Cell Tissue Res, 296.599-605, (1999).
Gu et al, "A Glu-496 to Ala Polymorphism leads to loss of function of the human P2X7 receptor," J Biol Chem, 276(14):11135-11142, (2001).
Gussow et al., "Humanization of Monoclonal Antibodies," Methods in Enzymology, 203:99-121, (1991).
Hansen et al., "Structural Motif and Characteristics of the Extracellular Domain of P2X Receptors," Biochem and Biophys Res Comm, 236(3):670-675, (1997).
Hansen et al., "The distribution of single P (2 x 1)—receptor clusters on smooth muscle cells in relation to nerve varicosities in the rat urinary bladder," J Neurocytol, 27(7): 529-539, (1998).
Holliger et al., "'Diabodies': Small bivalent and bispecific antibody fragments," Proc. Natl. Acad Sci. USA, 90:6444-6448, (1993).
Hopfner et al, "Expression of functional P2-purinergic receptors in primary cultures of human colorectal carcinoma cells," Biochem and Biophys Res Comm, 251:811-817, (1998).
Humphrey, "Gleason grading and prognostic factors in carcinoma of the prostate," Modern Pathology, 17:292-306, (2004).
Huston et al., "Protein engineering of antibody binding sites: Recovery of specific activity in an anti-digoxin single-chain Fv analogue produced in *Escherichia coli*," Proc. Natl. Acad. Sci. USA, 85:5879-5883, (1988).
Jacob et al., "Cytogenetic Profile of Chronic Myeloid Leukemias," Indian J Cancer, 39(2):61-65, (2002).
Jameison et al., "Extracellular ATP causes loss of L-selectin from human lymphocytes via occupancy of P2Z purinoceptors," J Cell Physiol, 166:637-642 (1996).
Janssens et al., "Effects of extracellular nucleotides and nucleosides on prostate carcinoma cells," Br J Pharmacol., 132: 536-46, (2001).
Jantzen et al., "Evidence for Two Distinct G-protein-coupled ADP Receptors Mediating Platelet Activation," Thromb and Haemost, 81:111-117, (1999).
Jones, "Critically assessing the state-of-the-art in protein structure prediction,"Pharmacogenomics Journal, 1:126-134, (2001).
Katzur et al., "Expression and responsiveness of P2Y2 receptors in human endometrial cancer cell lines," J Clin Endocrinol Metab., 84(11): 4085-4091, (1999).
Kennedy et al., "The discovery and development of P2 receptor subtypes," J Auto Nerv Syst, 81:158-163, (2000).
Kim et al., "Differential Assembly of Rat Purinergic P2X7 Receptor in Immune Cells of the Brain and Periphery," J Biol Chem, 276(26):23262-23267, (2001).
King et al., "Metabotropic receptors for ATP and UTP: exploring the correspondence between native and recombinant nucleotide receptors," TiPS, 19: 506-514, (1998).

Kishore et al., "Cellular localisation of P2Y2 purinoceptor in rat renal inner medulla and lung," Am J Physiol Renal Physiol, 278: F43-F51, (2000).

La Sala et al., "Alerting and tuning the immune response by extracellular Nucleotides," J Leukoc Biol, 73:339-343, (2003).

Lee et al., "P2X receptor immunoreactivity in the male genital organs of the rat," Cell Tissue Res, 300(2): 321-330, (2000).

Li et al., "P2X7 Receptor: A Novel Biomarker of Uterine Epithelial Cancers," Cancer Epidemiol Biomarkers Prev, 15(10):1906-1913, (2006).

Mager et al., "Prediction of the confirmation of the human P2X7 receptor," Letts Drug Des Discov, 3(10):675-682, (2006).

Maier et al., "Cloning of P2Y6 cDNAs and Identification of a Pseudogene: Comparison of P2Y Receptor Subtype Expression in Bone and Brain Tissues," Biochem and Biophys Res Comm, 237:297-302, (1997).

Mariuzza et al., "The structural basis of antigen-antibody recognition," Annual Review of Biophysics and Biophysical Chemistry, 16:139-159, (1987).

Mauro et al., "Chronic myelogenous leukaemia," Curr Opin Oncol, 13(1):3-7, (2001).

Meeker et al., "An additional breakpoint region in the BCL-1 locus associated with the t(11;14)(q13;q32) translocation of B-lymphocytic malignancy," Blood, 74:1801-1806, (1989).

Nawa et al., "Frequent loss of expression or aberrant alternative splicing of P2XM, a p53-inducible gene, in soft-tissue tumours," Br J Cancer, 80(8):1185-89, (1999).

Ngo et al., "Computational complexity, protein structure prediction, and the Levinthal paradox," In Merz and Le Grand (eds), The protein folding problem and tertiary structure prediction, Birkhauser: Boston, pp. 491-495, (1994).

Nihei et al., "Pharmacologic properties of P2z/P2X7 receptor characterized in murine dendritic cells: role on the induction of apoptosis", Blood, 96(3)996-1005, (2000).

Parr et al., "Cloning and expression of a human P2U nucleotide receptor, a target for cystic fibrosis pharmacotherapy," Proc. Natl. Acad. Sci. USA, 91:3275-3279, (1994).

Paul, Fundamental Immunology, Lippincott Williams & Wilkins, p. 107, (1998).

PCT International Preliminary Examination Report of Mar. 14, 2003 for application PCT/AU2001/001614.

PCT International Preliminary Examination Report of May 1, 2003 for application PCT/AU02/00061.

PCT International Preliminary Examination Report of Aug. 1, 2001 for application PCT/AU00/00363.

PCT International Preliminary Examination Report of Dec. 17, 2003 for application PCT/AU02/001204.

PCT International Preliminary Report on Patentability of Jan. 5, 2011 for application PCT/AU09/000869.

PCT International Preliminary Report on Patentability of Mar. 16, 2010 for application PCT/AU08/001364.

PCT International Preliminary Report on Patentability of Mar. 16, 2010 for application PCT/AU08/001365.

PCT International Preliminary Report on Patentability of Apr. 15, 2009 for application PCT/AU07/001540.

PCT International Preliminary Report on Patentability of Apr. 15, 2009 for application PCT/AU07/001541.

PCT International Preliminary Report on Patentability of Jun. 26, 2012 for application PCT/AU2010/001741.

PCT International Search Report for application PCT/AU2010/001741 mailed Feb. 11, 2011.

PCT International Search Report of Feb. 5, 2002 for application PCT/AU2001/001614.

PCT International Search Report of Apr. 2, 2002 for application PCT/AU02/00061.

PCT International Search Report of Jul. 21, 2000 for application PCT/AU00/00363.

PCT International Search Report of Aug. 7, 2009 for application PCT/AU09/000869.

PCT International Search Report of Sep. 22, 2010 for application PCT/AU10/001070.

PCT International Search Report of Oct. 14, 2002 for application PCT/AU02/001204.

PCT International Search Report of Oct. 27, 2008 for application PCT/AU08/001364.

PCT International Search Report of Nov. 9, 2007 for application PCT/AU07/001541.

PCT International Search Report of Nov. 21, 2008 for application PCT/AU08/001365.

PCT International Search Report of Nov. 2007 for application PCT/AU07/001540.

Peng et al., "P2Z purinoceptor, a special receptor for apoptosis induced by ATP in human leukemic lymphocytes," Chinese Med J, 112(4):356-362, (1999).

Perou et al., "Distinctive gene expression patterns in human mammary epithelial cells and breast cancers," Proc. Natl. Acad. Sci. USA, 96:9212-9217, (1999).

Poljak et al., "Production and structure of diabodies," Structure, 2:1121-1123, (1994).

Ralevic et al., "Receptors for Purines and Pyrimidines," Pharmacol Rev., 50(3):413-492, (1998).

Rassendren et al., "The permeabilizing ATP receptor, P2X7: Cloning and expression of a human cDNA," J Biol Chem, 272(9):5482-5486, (1997).

Ray et al., "Purinergic receptor distribution in endothelial cells in blood vessels: a basis for selection of coronary artery grafts," Atherosclerosis, 162:55-61, (2002).

Romagnoli et al., "Recent progress in the discovery of antagonists acting at P2X7 receptor," Expert Opinions Ther. Patents, 15(3):271-287, (2005).

Rudikoff et al., "Single amino acid substitution altering antigen-binding specificity," PNAS, 79:1979-1983, (1982).

Sauer et al., "Calcium-dependence of hydrogen peroxide-induced c-fos expression and growth stimulation of multicellular prostate tumour spheroids," FEBS Lett, 419: 201-205, (1997).

Schultze-Mosgau et al., "Characterization of calcium-mobilizing, purinergic P2Y2 receptors in human ovarian cancer cells," Mol Human Reproduct., 6(5): 435-442, (2000).

Slater et al. "Early prostate cancer detected using expression of non-functional cytolytic P2X7 receptors," Histopathology, 44:206-215, (2004).

Slater et al., "Detection of preneoplasia in histologically normal prostate biopsies," Prost Cancer Prostat Dis, 4:92-96, (2001).

Slater et al., "Differentiation between cancerous and normal hyperplastic lobules in breast lesions," Breast Cancer Res Treat, 83:1-10, (2004).

Slater et al., "Expression of the apoptotic calcium channel P2X7 in the glandular epithelium is a marker for early prostate cancer and correlates with increasing PSA levels," J Mol Histol., 36:159-165, (2005).

Slater et al., "Increased expression of apoptotic markers in melanoma," Melanoma Res, 13(2):137-145, (2003).

Slater et al., "Markers for the development of early prostate cancer," J Pathol,199:368-377, (2003).

Sluyter et al., "Extracellular ATP increases cation fluxes in human erthrocytes by activation of the P2X7 receptor," J Biol Chem, 279(43):44749-44756, (2004).

Spieker-Polet et al., "Rabbit monoclonal antibodies: Generating a fusion partner to produce rabbit-rabbit hybridomas," Proc. Natl. Acad. Sci USA, 92:9348-9352, (1995).

Supplementary European Search Report and European Search Opinion for application EP08800000 (published as EP2201026 ) mailed Oct. 29, 2012.

Supplementary European Search Report and European Search Opinion for application EP09771858 (published as EP2318438) mailed Oct. 24, 2012.

Supplementary European Search Report of Mar. 4, 2011 for application EP01270623 (published as EP1352085).

Supplementary European Search Report of May 21, 2010 for application EP07815345 (published as EP2082032).

Supplementary European Search Report of Aug. 16, 2010 for application EP08800001 (published as EP2201377).

Supplementary European Search Report of Nov. 8, 2002 for application EP00918600 (published as EP1179183).

Supplementary Partial European Search Report of Apr. 29, 2005 for application EP02715313 (published as EP1360203).

Surprenant et al., "The cytosolic P2Z receptor for extracellular ATP identified as a P2X receptor (P2X7)," Science, 272:735-738, (1996).
Tockman et al., "Considerations in Bringing a Cancer Biomarker to Clinical Application," Cancer Res, 52:2711s-2718s, (1992).
Torres et al., "Hetero-oligomeric Assembly of P2X Receptor Subunits," J Biol Chem, 274(10):6653-6659, (1999).
Tosatto et al., "Large-Scale Prediction of Protein Structure and Function from Sequence," Current Pharmaceutical Design, 12:2067-2086, (2006).
U.S. Appl. No. 10/019,356 (now Patent No. 7,183,064), Final Office Action mailed May 9, 2006.
U.S. Appl. No. 10/019,356 (now Patent No. 7,183,064), Non-Final Office Action mailed Jul. 19, 2005.
U.S. Appl. No. 10/019,356 (now Patent No. 7,183,064), Notice of Allowance mailed Oct. 11, 2006.
U.S. Appl. No. 10/019,356 (now Patent No. 7,183,064), Requirement for Restriction/Election mailed Mar. 18, 2005.
U.S. Appl. No. 10/450,205 (now Abandoned, Publication No. 2004/0067542), Final Office Action mailed Sep. 7, 2007.
U.S. Appl. No. 10/450,205 (now Abandoned, Publication No. 2004/0067542), Non-Final Office Action mailed Dec. 19, 2006.
U.S. Appl. No. 10/450,205 (now Abandoned, Publication No. 2004/0067542), Requirement for Restriction/Election mailed Sep. 6, 2006.
U.S. Appl. No. 10/622,313 (now Patent No. 7,326,415), Non-Final Office Action mailed Nov. 30, 2006.
U.S. Appl. No. 10/622,313 (now Patent No. 7,326,415), Notice of Allowance and Examiner Interview Summary Record mailed Sep. 5, 2007.
U.S. Appl. No. 10/622,313 (now Patent No. 7,326,415), Requirement for Restriction/Election mailed Jun. 16, 2006.
U.S. Appl. No. 11/566,472 (now Abandoned, Publication No. 2007/0248963), Examiner Interview Summary Record mailed Dec. 30, 2009.
U.S. Appl. No. 11/566,472 (now Abandoned, Publication No. 2007/0248963), Final Office Action mailed Jan. 12, 2009.
U.S. Appl. No. 11/566,472 (now Abandoned, Publication No. 2007/0248963), Final Office Action mailed Mar. 9, 2010.
U.S. Appl. No. 11/566,472 (now Abandoned, Publication No. 2007/0248963), Non-Final Office Action mailed Jun. 16, 2008.
U.S. Appl. No. 11/566,472 (now Abandoned, Publication No. 2007/0248963), Non-Final Office Action mailed Aug. 26, 2009.
U.S. Appl. No. 11/566,472 (now Abandoned, Publication No. 2007/0248963), Requirement for Restriction/Election mailed Dec. 17, 2007.
U.S. Appl. No. 11/968,607 (now Patent No. 7,531,171), Non-Final Office Action mailed Sep. 26, 2008.
U.S. Appl. No. 11/968,607 (now Patent No. 7,531,171), Notice of Allowance mailed Jan. 9, 2009.
U.S. Appl. No. 11/968,607 (now Patent No. 7,531,171), Requirement for Restriction/Election mailed Aug. 19, 2008.
U.S. Appl. No. 12/043,083 (now Abandoned, Publication No. 2008/0227122), Non-Final Office Action mailed Nov. 26, 2010.
U.S. Appl. No. 12/043,083 (now Abandoned, Publication No. 2008/0227122), Notice of Allowance mailed Aug. 5, 2011.
U.S. Appl. No. 12/043,083 (now Abandoned, Publication No. 2008/0227122), Requirement for Restriction/Election mailed Jul. 21, 2010.
U.S. Appl. No. 12/417,989 (now Patent No. 7,888,473), Non-Final Office Action mailed Jun. 16, 2010.
U.S. Appl. No. 12/417,989 (now Patent No. 7,888,473), Notice of Allowance mailed Sep. 24, 2010.
U.S. Appl. No. 12/445,258 (now Abandoned, Publication No. 2010/0036101), Non-Final Office Action mailed Oct. 18, 2011.
U.S. Appl. No. 12/445,258 (now Abandoned, Publication No. 2010/0036101), Requirement for Restriction/Election mailed May 6, 2011.
U.S. Appl. No. 12/445,273 (now Patent No. 8,067,550), Non-Final Office Action mailed Oct. 1, 2010.
U.S. Appl. No. 12/445,273 (now Patent No. 8,067,550), Notice of Allowance mailed Mar. 30, 2011.
U.S. Appl. No. 12/445,273 (now Patent No. 8,067,550), Notice of Allowance mailed Jul. 8, 2011.
U.S. Appl. No. 12/445,273 (now Patent No. 8,067,550), Requirement for Restriction/Election mailed Aug. 9, 2010.
U.S. Appl. No. 12/677,795 (now Patent No. 8,293,491), Notice of Allowance mailed Jun. 22, 2012.
U.S. Appl. No. 12/677,795 (now Patent No. 8,293,491), Restriction/Election Requirement mailed Oct. 12, 2011.
U.S. Appl. No. 12/878,865 (now Abandoned, Publication No. 2011/0111431), Non-Final Office Action mailed Oct. 20, 2011.
U.S. Appl. No. 12/878,865 (now Abandoned, Publication No. 2011/0111431), Requirement for Restriction/Election mailed Mar. 25, 2011.
U.S. Appl. No. 12/975,341 (now Patent No. 8,080,635), Non-Final Office Action mailed Mar. 24, 2011.
U.S. Appl. No. 12/975,341 (now Patent No. 8,080,635), Notice of Allowance mailed Aug. 17, 2011.
U.S. Appl. No. 13/002,647, Requirement for Restriction/Election mailed Aug. 7, 2012.
U.S. Appl. No. 13/298,222, Final Office Action mailed Sep. 7, 2012.
U.S. Appl. No. 13/298,222, Non-Final Office Action mailed Feb. 13, 2012.
U.S. Appl. No. 13/298,222, Notice of Allowance and Examiner Interview Summary Record mailed Nov. 27, 2012.
U.S. Appl. No. 12/677,795 (now Patent No. 8,293,491), Non-Final Office Action mailed Feb. 29, 2012.
Uniprot entry Q4VKI0_Human P2X7 Isoform E, UniProt Consortium, (2005).
Uniprot entry Q4VKI1_Human P2X7 Isoform F, UniProt Consortium, (2005).
Urano et al., "Cloning of P2XM, a novel human P2X receptor gene regulated by p53," Cancer Res, 57:3281-87, (1997).
Virginio et al., "Kinetics of cell lysis, dye uptake and permeability changes in cells expressing the rat P2X7 receptor," J Physiol., 519(2):335-346, (1999).
von Kugelgen et al., "Molecular Pharmacology of P2Y-receptors," Naunyn Scmiedebergs Arch Pharmacol, 362:(4-5)310-323, (2000).
Vulchanova et al., "Immunohistochemical study of the P2X2 and P2X3 receptor subunits in rat and monkey sensory neurons and their central terminals," Neuropharmacol, 36(9):1229-1242, (1997).
Wagstaff et al ., "Extracellular ATP activates multiple signalling pathways and potentiates growth factor-induced c-fos gene expression in MCF-7 breast cancer cells," Carcinogenesis 21(12):2175-2181, (2000).
Wang et al., "P2X7 receptor-mediated apoptosis of human cervical epithelial cells," Am. J Physiol, 287:1349-1358, (2004).
Ward et al., "Binding activities of a repertoire of single immunoglobulin variable domains secreted from *Escherichia coli*," Nature 341:544-546, (1989).
Wasilenko et al., "Calcium signaling in prostate cancer cells: Evidence for multiple receptors and enhanced sensitivity to bombesin/GRP," The Prostate 30:167-173 (1997).
Wells "Additivity of mutational effects in proteins," Biochemistry, 29(37):8509-8517, (1990).
White et al., "P2Y purinergic receptors regulate the growth of human melanomas," Cancer Letts, 224:81-91, (2005).
Wiley et al., "A single nucleotide polymorphism is associated with loss of function of the monocyte P2X7 receptor," Blood, 96(11):17, (2000). Abstract.
Wiley et al., "Genetic polymorphisms of the human P2X7 receptor and relationship to function," Drug Dev Res, 53(2-3):72-76, (2001).
Williams et al., "Purinergic and pyrimidinergic receptors as potential drug targets," Biochem Pharm, 59:1173-1184, (2000).
Winkler et al., "Changing the antibody binding specificity by single point mutations of an Anti-p24 (HIV-1) antibody," Journal of Immunology, 165:4505-4514, (2000).
Wurl et al., "High prognostic significance of Mdm2/p53 co-overexpression in soft tissue sarcomas of the extremities," Oncogene, 16(9):1183-85, (1998).

* cited by examiner

Figure 1: SEQ ID NO:1

```
1    MPACCSCSDV FQYETNKVTR IQSMNYGTIK WFFHVIIFSY VCFALVSDKL YQRKEPVISS

61   VHTKVKGIAE VKEEIVENGV KKLVHSVFDT ADYTFPLQGN SFFVMTNFLK TEGQEQRLCP

121  EYPTRRTLCS SDRGCKKGWM DPQSKGIQTG RCVVHEGNQK TCEVSAWCPI EAVEEAPRPA

181  LLNSAENFTV LIKNNIDFPG HNYTTRNILP GLNITCTFHK TQNPQCPIFR LGDIFRETGD

241  NFSDVAIQGG IMGIEIYWDC NLDRWFHHCR PKYSFRRLDD KTTNVSLYPG YNFRYAKYYK

301  ENNVEKRTLI KVFGIRFDIL VFGTGGKFDI IQLVVYIGST LSYFGLAAVF IDFLIDTYSS

361  NCCRSHIYPW CKCCQPCVVN EYYYRKKCES IVEPKPTLKY VSFVDESHIR MVNQQLLGRS

421  LQDVKGQEVP RPAMDFTDLS RLPLALHDTP PIPGQPEEIQ LLRKEATPRS RDSPVWCQCG

481  SCLPSQLPES HRCLEELCCR KKPGACITTS ELFRKLVLSR HVLQFLLLYQ EPLLALDVDS

541  TNSRLRHCAY RCYATWRFGS QDMADFAILP SCCRWRIRKE FPKSEGQYSG FKSPY
```

Figure 2: SEQ ID NO:2

KYYKENNVEKRTLIKVF

Figure 3: SEQ ID NO:3

KTTNVSLYPGYNFRYAKYYKENNVEKRTLIKVFGIRFDILVFGTGGKFD

Figure 4: SEQ ID NO:4

```
                              MTPGDHSWGN SFFVMTNFLK TEGQEQRLCP

121   EYPTRRTLCS SDRGCKKGWM DPQSKGIQTG RCVVHEGNQK TCEVSAWCPI EAVEEAPRPA

181   LLNSAENFTV LIKNNIDFPG HNYTTRNILP GLNITCTFHK TQNPQCPIFR LGDIFRETGD

241   NFSDVAIQGG IMGIEIYWDC NLDRWFHHCR PKYSFRRLDD KTTNVSLYPG YNFRYAKYYK

301   ENNVEKRTLI KVFGIRFDIL VFGTGGKFDI IQLVVYIGST LSYFGLAAVF IDFLIDTYSS

361   NCCRSHIYPW CKCCQPCVVN EYYYRKKCES IVEPKPTLKY VSFVDESHIR MVNQQLLGRS

421   LQDVKGQEVP RPAMDFTDLS RLPLALHDTP PIPGQPEEIQ LLRKEATPRS RDSPVWCQCG

481   SCLPSQLPES HRCLEELCCR KKPGACITTS ELFRKLVLSR HVLQFLLLYQ EPLLALDVDS

541   TNSRLRHCAY RCYATWRFGS QDMADFAILP SCCRWRIRKE FPKSEGQYSG FKSPY
```

Figure 5: SEQ ID NO:5

```
                                                             MDGPAEQRPA

181    LLNSAENFTV  LIKNNIDFPG  HNYTTRNILP  GLNITCTFHK  TQNPQCPIFR  LGDIFRETGD

241    NFSDVAIQGG  IMGIEIYWDC  NLDRWFHHCR  PKYSFRRLDD  KTTNVSLYPG  YNFRYAKYYK

301    ENNVEKRTLI  KVFGIRFDIL  VFGTGGKFDI  IQLVVYIGST  LSYFGLAAVF  IDFLIDTYSS

361    NCCRSHIYPW  CKCCQPCVVN  EYYYRKKCES  IVEPKPTLKY  VSFVDESHIR  MVNQQLLGRS

421    LQDVKGQEVP  RPAMDFTDLS  RLPLALHDTP  PIPGQPEEIQ  LLRKEATPRS  RDSPVWCQCG

481    SCLPSQLPES  HRCLEELCCR  KKPGACITTS  ELFRKLVLSR  HVLQFLLLYQ  EPLLALDVDS

541    TNSRLRHCAY  RCYATWRFGS  QDMADFAILP  SCCRWRIRKE  FPKSEGQYSG  FKSPY
```

Figure 6: SEQ ID NO:6

```
1      MPACCSCSDV  FQYETNKVTR  IQSMNYGTIK  WFFHVIIFSY  VCFALVSDKL  YQRKEPVISS

61     VHTKVKGIAE  VKEEIVENGV  KKLVHSVFDT  ADYTFPLQGN  SFFVMTNFLK  TEGQEQRLCP

121    EYPTRRTLCS  SDRGCKKGWM  DPQSKGIQTG  RCVVHEGNQK  TCEVSAWCPI  EAVEEAPRPA

181    LLNSAENFTV  LIKNNIDFPG  HNYTTRNILP  GLNITCTFHK  TQNPQCPIFR  LGDIFRETGD

241    NFSDVAIQGG  IMGIEIYWDC  NLDRWFHHCR  PKYSFRRLDD  KTTNVSLYPG  YNFRYAKYYK

301    ENNVEKRTLI  KVFGIRFDIL  VFGTGGKFDI  IQLVVYIGST  LSYFGLVRDS  EGSD
```

Figure 7: SEQ ID NO:7

M WQFRYAKYYK

301    ENNVEKRTLI KVFGIRFDIL VFGTGGKFDI IQLVVYIGST LSYFGLAAVF IDFLIDTYSS

361    NCCRSHIYPW CKCCQPCVVN EYYYRKKCES IVEPKPTLKY VSFVDESHIR MVNQQLLGRS

421    LQDVKGQEVP RPAMDFTDLS RLPLALHDTP PIPGQPEEIQ LLRKEATPRS RDSPVWCQCG

481    SCLPSQLPES HRCLEELCCR KKPGACITTS ELFRKLVLSR HVLQFLLLYQ EPLLALDVDS

541    TNSRLRHCAY RCYATWRFGS QDMADFAILP SCCRWRIRKE FPKSEGQYSG FKSPY

Figure 8: SEQ ID NO:8

1      MPACCSCSDV FQYETNKVTR IQSMNYGTIK WFFHVIIFSY VCFALVSDKL YQRKEPVISS

61     VHTKVKGIAE VKEEIVENGV KKLVHSVFDT ADYTFPLQGN SFFVMTNFLK TEGQEQRLCP

121    EYPTRRTLCS SDRGCKKGWM DPQSKGIQTG RCVVHEGNQK TCEVSAWCPI EAVEEAPRPA

181    LLNSAENFTV LIKNNIDFPG HNYTT

241                                                                YAKYYK

301    ENNVEKRTLI  KVFGIRFDIL  VFGTGGKFDI  IQLVVYIGST  LSYFGLVRDS  LFHALGKWFG
361    EGSD

Figure 9: SEQ ID NO:9

```
 61                                         MTPGDHSWGN SFFVMTNFLK TEGQEQRLCP

121     EYPTRRTLCS SDRGCKKGWM DPQSKGIQTG RCVVHEGNQK TCEVSAWCPI EAVEEAPRPA

181     LLNSAENFTV LIKNNIDFPG HNYTTRNILP GLNITCTFHK TQNPQCPIFR LGDIFRETGD

241     NFSDVAIQGG IMGIEIYWDC NLDRWFHHCR PKYSFRRLDD KTTNVSLYPG YNFRYAKYYK

301     ENNVEKRTLI   KVFGIRFDIL   VFGTGGKFDI   IQLVVYIGST   LSYFGLVRDS   LFHALGKWFG
361     EGSD
```

Figure 10: SEQ ID NO:10

```
  1     MPACCSCSDV FQYETNKVTR IQSMNYGTIK WFFHVIIFSY VCFALVSDKL YQRKEPVISS

61     VHTKVKGIAE VKEEIVENGV KKLVHSVFDT ADYTFPLQGN SFFVMTNFLK TEGQEQRLCP

121     EYPTRRTLCS SDRGCKKGWM DPQSKGIQTG RCVVHEGNQK TCEVSAWCPI EAVEEAPRPA

181     LLNSAENFTV LIKNNIDFPG HNYTTRNILP GLNITCTFHK TQNPQCPIFR LGDIFRETGD

241     NFSDVAIQIR QVLQGKQC
```

Figure 11: SEQ ID NO:11

```
1    MPACCSCSDV FQYETNKVTR IQSMNYGTIK WFFHVIIFSY VCFALVSDKL YQRKEPVISS

61   VHTKVKGIAE VKEEIVENGV KKLVHSVFDT ADYTFPLQGN SFFVMTNFLK TEGQEQRLCP

121  EEFRPEGV
```

Figure 12: SEQ ID NO:12

GHNYTTRNILPGLNITC

P2X7 EPITOPES

CROSS-REFERENCES TO RELATED APPLICATIONS

This application is a U.S. National Stage Application of PCT/AU2008/001364, filed Sep. 12, 2008, which claims priority to Australian patent application number 2007905018, filed Sep. 14, 2007, the contents of which are herein incorporated by reference in their entirety.

FIELD OF THE INVENTION

The invention relates to purinergic (P2X) receptors, to generation of antibodies and to use of antibodies and immunogens for detection and treatment of a disease or condition, especially cancer.

BACKGROUND OF THE INVENTION

Purinergic (P2X) receptors are ATP-gated cation—selective channels. Each receptor is made up of three protein subunits or monomers. To date seven separate genes encoding P2X monomers have been identified: P2X1, P2X2, P2X3, P2X4, P2X5, P2X6, P2X7.

P2X7 receptors are of particular interest as the expression of these receptors is understood to be limited to cells having potential to undergo programmed cell death, such as thymocytes, dendritic cells, lymphocytes, macrophages and monocytes. There is some expression of P2X7 receptors in normal homeostasis, such as on erythrocytes.

Interestingly, a P2X7 receptor containing one or more monomers having a cis isomerisation at Pro210 (according to SEQ ID NO: 1 in FIG. 1) and which is devoid of ATP binding function has been found on cells that are understood to be unable to undergo programmed cell death, such as preneoplastic cells and neoplastic cells.

Antibodies generated from immunisation with a peptide including Pro210 in cis bind to P2X7 receptors that are devoid of ATP binding function. However, they do not bind to P2X7 receptors capable of binding ATP. Accordingly, these antibodies are useful for selectively detecting many forms of carcinoma and haemopoietic cancers and to treatment of some of these conditions.

The region of the P2X7 receptor containing Pro210 forms part of the extra cellular domain of the receptor. Antibodies raised against other epitopes on this domain, including those that bind regions including from Val71 to Val87 (according to SEQ ID NO: 1 in FIG. 1) and from Lys 137 to Cys152 (according to SEQ ID NO:1 in FIG. 1) have been found not to be capable of selectively binding to the receptor that is devoid of ATP binding function. Hence, other than the antibodies directed to the region including Pro210, no other antibodies have been found to date to be able to discriminate between ATP and non ATP binding receptors.

There is a need for reagents for detection of cancer and in this context, for new antibodies capable of discriminating between ATP and non ATP binding P2X7 receptors. There is also a need for new cancer therapeutics, including antibodies and immunogens for providing an anti tumour response.

SUMMARY OF THE INVENTION

In certain embodiments there is provided a peptide:
consisting of the sequence of SEQ ID NO: 2;
consisting of a sequence within the sequence of SEQ ID NO: 2, said peptide being useful as an immunogen to generate an antibody that is capable of selectively binding to a non ATP-binding P2X7 receptor but not to an ATP-binding P2X7 receptor;
consisting of a sequence of SEQ ID NO: 3, said peptide being useful as an immunogen to generate an antibody that is capable of selectively binding to a non ATP-binding P2X7 receptor but not to an ATP-binding P2X7 receptor; or
consisting of a sequence within the sequence of SED ID NO: 3, said peptide being useful as an immunogen to generate an antibody that is capable of selectively binding to a non ATP-binding P2X7 receptor but not to an ATP-binding P2X7 receptor.

In other embodiments there is provided an antibody or fragment thereof:
capable of binding to a peptide described above; or
capable of binding to an epitope that includes one or more residues of a peptide having a sequence of SEQ ID NO: 2.

In other embodiments there is provided an immune complex formed from the binding of an antibody or fragment thereof described above to a non ATP-binding P2X7 receptor, monomer or fragment thereof, or to a peptide as described above.

In certain embodiments there is provided a method for determining whether a cell, tissue or extra cellular body fluid includes a non ATP-binding P2X7 receptor, monomer or fragment thereof including:
contacting a cell, tissue or extra cellular body fluid with an antibody or fragment thereof in conditions for forming an immune complex as described above, and
detecting whether an immune complex has been formed, wherein detection of an immune complex determines that a cell, tissue or extra-cellular body fluid includes a non ATP-binding P2X7 receptor, monomer or fragment thereof.

In other embodiments there is provided a method for determining whether a cell, tissue or extra-cellular body fluid contains an antibody against a non ATP-binding P2X7 receptor, monomer or fragment thereof including:
contacting a cell, a tissue or an extra-cellular body fluid with a peptide as described above in conditions for forming an immune complex between the peptide and an antibody in the cell, tissue or extra-cellular body fluid, and
detecting whether an immune complex has been formed, wherein detection of an immune complex determines that a cell, tissue or extra-cellular body fluid contains an antibody against a non ATP-binding P2X7 receptor, monomer or fragment thereof.

In yet further embodiments there is provided a kit or composition for determining whether a cell, tissue or extra-cellular body fluid contains a non ATP-binding P2X7 receptor, monomer or fragment thereof, or an antibody against same including:
a peptide as described above; and/or
an antibody or fragment thereof as described above; and/or
non ATP-binding P2X7 receptor, monomer or fragment thereof; and optionally
a further antibody for binding to the peptide, antibody or fragment thereof or the non ATP-binding P2X7 receptor, monomer or fragment thereof;
written instructions for use of the kit in a method described above.

In other embodiments there is provided a pharmaceutical composition including an antibody or fragment thereof as described above, or a peptide as described above together with a pharmaceutically acceptable carrier, diluent or excipient.

In related embodiments there is provided a method of treatment of a disease characterised by the expression of a non ATP-binding P2X7 receptor, monomer or fragment thereof including the step of providing an antibody or fragment thereof as described above, or a peptide as described above to an individual requiring said treatment.

BRIEF DESCRIPTION OF THE FIGURES

FIG. 1 shows SEQ ID NO:1.
FIG. 2 shows SEQ ID NO:2.
FIG. 3 shows SEQ ID NO:3.
FIG. 4 shows SEQ ID NO:4.
FIG. 5 shows SEQ ID NO:5.
FIG. 6 shows SEQ ID NO:6.
FIG. 7 shows SEQ ID NO:7.
FIG. 8 shows SEQ ID NO:8.
FIG. 9 shows SEQ ID NO:9.
FIG. 10 shows SEQ ID NO:10.
FIG. 11 shows SEQ ID NO:11.
FIG. 12 shows SEQ ID NO:12.

DETAILED DESCRIPTION OF THE EMBODIMENTS

For the following descriptions, the technical and scientific terms used herein will have the meanings commonly understood by one of ordinary skill in the art, unless specifically defined otherwise.

The inventors have identified an epitope that is exclusively expressed on non ATP-binding P2X7 receptors (otherwise known as "non functional receptors"). The epitope and peptides including the epitope have been found to be useful for generating antibodies and immune complexes that indicate the presence or absence or predisposition to a variety of diseases and conditions including carcinoma.

Thus in certain embodiments there is provided a peptide consisting of the sequence: SEQ ID NO: 2: KYYKENNVEKRTLIKVF The peptide may consist of a sequence within the sequence of SEQ ID NO: 2 (FIG. 2), in which case the peptide can be used as an immunogen to generate an antibody that is capable of selectively binding to a non ATP-binding P2X7 ("non-functional") receptor but not to an ATP-binding P2X7 ("functional") receptor. The term "non ATP-binding" and "non-functional" in relation to P2X7 may be used interchangeably in the specification and claims. Similarly, the term "ATP-binding" and "functional" may be used interchangeably in the specification and claims.

Generally a non ATP-binding receptor means a trimer or higher multimer formed from at least one P2X7 monomer, the trimer or higher multimer being at least substantially devoid of ATP binding activity. In certain embodiments, these trimers or higher multimers are substantially unable to form a pore in a cell membrane for ingress of calcium cations into the cell cytoplasm.

Methods for screening peptides that can be used as an immunogen to generate an antibody that is capable of selectively binding to a non ATP-binding P2X7 receptor but not to an ATP-binding P2X7 receptor are disclosed herein. One example includes the use of erythrocytes in a rosetting assay. In this assay an antibody that binds to functional receptors is used as a positive control in which rossettes are observed. A test antibody is determined not to bind to functional receptors if it fails to form rossettes. It is determined to bind to non functional receptors if it is observed to bind to a non functional receptor-expressing cell line, including those discussed herein.

In these embodiments, the peptide may have a length of 6, 7, 8, 9, 10, 11, 12, 13, 14, 15, 16 or 17 residues.

In other embodiments, the peptide consists of a sequence of SEQ ID NO: 3 (FIG. 3), said peptide being useful as an immunogen to generate an antibody that is capable of selectively binding to a non ATP-binding P2X7 receptor but not to an ATP-binding P2X7 receptor.

The peptide may consist of a sequence within the sequence of SEQ ID NO: 3, said peptide being useful as an immunogen to generate an antibody that is capable of selectively binding to a non ATP-binding P2X7 receptor but not to an ATP-binding P2X7 receptor. Examples of these peptides include those having a sequence described in Table 1 (numbering according to SEQ ID NO: 1):

TABLE 1

| | |
|---|---|
| K281 to K297 | Y298 to G314 |
| T282 to Y298 | Y299 to I315 |
| T283 to Y299 | K300 to R316 |
| N284 to K300 | E301 to F317 |
| V285 to E301 | N302 to D318 |
| S286 to N302 | N303 to I319 |
| L287 to N303 | V304 to L320 |
| Y288 to V304 | E305 to V321 |
| P289 to E305 | K306 to F322 |
| G290 to K306 | R307 to G323 |
| Y291 to R307 | T308 to T324 |
| N292 to T308 | L309 to G325 |
| F293 to L309 | I310 to G326 |
| R294 to I310 | K311 to K327 |
| Y295 to K311 | V312 to F328 |
| A296 to V312 | F313 to D329 |
| K297 to F313 (SEQ ID NO: 2) | |

The peptide shown in Table 1 may have a length of from 6, 7, 8, 9, 10, 11, 12, 13, 14, 15, 16 or 17 residues.

In other embodiments there is provided an antibody or fragment thereof capable of binding to a peptide described above.

The antibody may be produced by immunisation with a peptide as described above. An example of a suitable immunisation is described in Example 1 below.

The antibody may also be produced by immunisation with a non ATP-binding P2X7 receptor, such as a receptor having an amino acid sequence shown in SEQ ID NO: 1, or a fragment thereof including the amino acid sequences SEQ ID NOS: 3 to 9 (shown in FIGS. 3 to 9).

In one embodiment, the non ATP-binding P2X7 receptor, monomer or fragment thereof used for the immunisation has Pro210 in cis isomerisation.

The antibody may bind to an epitope that includes one or more residues of a peptide having a sequence of SEQ ID NO: 2. In certain embodiments, the antibody binds to K297 or Y298 or Y299 or K300 or E301 or N302 or N303 or V304 or E305 or K306 or R307 or T308 or L309 or I310 or K311 or V312 or F313

The epitope may include a sequence of residues of a peptide having a sequence of SEQ ID NO: 2. In certain embodiments, the antibody binds to a sequence including K297 and Y298, or Y298 and Y299, or Y299 and K300, or K300 and E301, or E301 and N302, or N302 and N303, or N303 and V304, or V304 and E305, or E305 and K306, or K306 and R307, or R307 and T308, or T308 and L309, or L309 and I310, or I310 and K311, or K311 and V312, or V312 and F313.

The antibody that binds to one or more of the above residues may also bind to one or more residues of the P2X7 receptor extra cellular domain that are located outside of the region defined by SEQ ID NO:3. For example, the one or more residues located outside of the region defined by SEQ ID NO:3 may be located in a sequence of amino acid residues of an ATP-binding P2X7 receptor that defines the ATP binding site of the ATP-binding P2X7 receptor.

In one embodiment, the one or more residues located outside the sequence of SEQ ID NO:3 may be located in the sequence of SEQ ID NOS: 10 to 12 (FIGS. 10 to 12 respectively).

The antibody may be a whole antibody of any isotype. The antibody may be one obtained from monoclonal or polyclonal antisera. The antibody may be produced by hybridoma, or by recombinant expression.

The antibody may be chimeric, i.e. one containing human variable domains and non human constant domains. Alternatively, it may be humanized, i.e one formed by grafting non human CDRs onto a human antibody framework. Still further, the antibody may be fully human.

The antibodies of the invention may be modified with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). Homodimeric antibodies with enhanced anti-tumor activity can also be prepared using heterobifunctional cross-linkers. Alternatively, an antibody can be engineered that has dual Fc regions and can thereby have enhanced complement lysis and ADCC capabilities.

Where the antibody is an antibody fragment, the antibody fragment is selected from the group consisting of a dAb, Fab, Fd, Fv, F(ab')2, scFv and CDR.

The antibody or fragment may be provided on a solid phase such as a bead, surface or tissue culture vessel.

The antibody or fragment thereof may be provided with a label for detection of binding of the antibody or fragment thereof to antigen.

The antibodies and fragments may be labelled for use in medical imaging. Such methods involve chemical attachment of a labelling or imaging agent, such as a radioisotope, which include 67 Cu, 90 Y, 124 I, 125 I, 131 I, 186 Re, 188Re, 211 At, 212 Bi, administration of the labelled antibody or fragment to a subject in an acceptable carrier, and imaging the labelled antibody or fragment in vivo at the target site. Radiolabelled antibodies or fragments thereof may be particularly useful in in vivo imaging of cancers described herein.

The antibodies can be purified by methods known to the skilled artisan. Purification methods include, among other, selective precipitation, liquid chromatography, HPLC, electrophoresis, chromatofocusing, and various affinity techniques.

In some embodiments, the antibodies disclosed herein may also include multimeric forms of antibodies. For example, antibodies of the invention may take the form of antibody dimers, trimers, or higher-order multimers of monomeric immunoglobulin molecules.

Crosslinking of antibodies can be done through various methods known in the art. For example, crosslinking of antibodies may be accomplished through natural aggregation of antibodies, through chemical or recombinant linking techniques or other methods known in the art. For example, purified antibody preparations can spontaneously form protein aggregates containing antibody homodimers, and other higher-order antibody multimers. In a specific embodiment, crosslinking of antibodies by using a second antibody to bind to the antibodies of interest can be used to form a homodimer. The crosslinker antibody can be derived from a different animal compared to the antibody of interest. For example, a goat anti-mouse antibody (Fab specific) may be added to a mouse monoclonal antibody to form a homodimer. This bivalent crosslinker antibody recognizes the Fab or Fc region of the two antibodies of interest forming a homodimer.

Alternatively, antibody homodimers may be formed through chemical linkage techniques known in the art. Chemical crosslinkers can be homo or heterobifunctional and will covalently bind with two antibodies forming a homodimer. In some embodiments, it is desirable that the chemical crosslinker not interact with the antigen-binding region of the antibody as this may affect antibody function. As will be appreciated by those skilled in the art, antibodies can be crosslinked at the Fab region.

In one embodiment there is provided an immune complex formed from the binding of an antibody or fragment thereof as described above to a non ATP-binding (i.e. non-functional) P2X7 receptor, monomer or fragment thereof. In one embodiment there is provided an immune complex formed from the binding of an antibody or fragment thereof to a peptide described above.

Generally an immune complex otherwise known as an antigen-antibody complex is a product that is formed from the binding of an antibody via an antibody binding site to an epitope on an antigen against which the antibody is raised. The complex may or may not consist of more than one antibody.

The immune complex is particularly important as detection of this in vitro or in vivo is indicative of presence of, or predisposition to a disease or condition including preneoplasia and neoplasia. These detection methods are described in more detail below.

The non-ATP binding P2X7 receptor, monomer or fragment thereof included in the immune complex may have Pro210 in cis isomerisation.

The non-ATP binding P2X7 receptor, monomer or fragment thereof included in the immune complex may have an amino acid sequence of any one of SEQ ID NOS: 4 to 9 or fragments thereof.

The non-ATP binding P2X7 receptor, monomer or fragment thereof included in the immune complex may have a molecular weight in the range of from about 15 to 80 kDa.

The non-ATP binding P2X7 receptor, monomer or fragment thereof included in the immune complex may lack a transmembrane domain.

The immune complex may be formed by binding a non-ATP binding P2X7 receptor, monomer or fragment thereof located on a cell surface membrane, in a cytoplasm, in a nucleus or in extra-cellular fluid. The extra-cellular fluid may be blood, plasma, serum, lymph, urine, semen, saliva, sputum, ascites, faeces, uterine and vaginal secretions, bile, amniotic fluid, cerebrospinal fluid and organ and tissue flushings.

The antibody or antibody fragment included in the immune complex may be attached to a solid phase, such as a bead or a plate, so that the immune complex is attached to a solid phase when formed. Alternatively, the non-ATP binding P2X7 receptor, monomer or fragment thereof included in the immune complex may be attached to a solid phase.

The antibody may be labelled for detection of formation of the immune complex.

The immune complex may further include an antibody or fragment thereof, such as a capture antibody for capture of the immune complex. The further antibody or fragment thereof may bind to the anti P2X7 receptor antibody. Also, the further antibody or fragment thereof may bind to the receptor or fragment thereof.

The further antibody or fragment thereof may be bound to a solid phase such as a phase described above.

The further antibody may be labelled for detection of formation of the immune complex. Examples of labels include fluorophores, dyes, isotopes etc.

In certain embodiments there is provided a method for determining whether a cell, tissue or extra cellular body fluid includes a non ATP-binding P2X7 receptor, monomer or fragment thereof including:
    contacting a cell, tissue or extra cellular body fluid with an antibody or fragment thereof in conditions for forming an immune complex as described above, and
    detecting whether an immune complex has been formed, wherein detection of an immune complex determines that a cell, tissue or extra-cellular body fluid includes a non ATP-binding P2X7 receptor, monomer or fragment thereof.

In other embodiments there is provided a use of an antibody or fragment thereof described above in the manufacture of means for determining whether a cell, tissue or extra-cellular body fluid contains a P2X7 receptor, monomer or fragment thereof.

In other embodiments there is provided a method for determining whether a cell, tissue or extra-cellular body fluid contains an antibody against a non ATP-binding P2X7 receptor, monomer or fragment thereof including:
    contacting a cell, a tissue or an extra-cellular body fluid with a peptide as described above in conditions for forming an immune complex between the peptide and an antibody in the cell, tissue or extra-cellular body fluid, and
    detecting whether an immune complex has been formed, wherein detection of an immune complex determines that a cell, tissue or extra-cellular body fluid contains an antibody against a non ATP-binding P2X7 receptor, monomer or fragment thereof.

In other embodiments there is provided a use of a peptide described above in the manufacture of means for determining whether a cell, tissue or extra-cellular body fluid contains an antibody against a non ATP-binding P2X7 receptor, monomer or fragment thereof.

The presence of a given protein, or level of expression of a given protein in a host cell, tissue or extra-cellular body fluid can be detected by any number of assays. Examples include immunoassays, chromatography and mass spectrometry.

Immunoassays, i.e. assays involving an element of the immune system are particularly preferred. These assays may generally be classified into one of:
(i) assays in which purified antigen is used to detect an antibody in host serum. For example, purified antigen is bound to solid phase by adsorption or indirectly through another molecule and host serum is applied followed by another antibody for detecting presence or absence of host antibody;
(ii) assays in which purified antigen is used to detect immune cells, such as T and B lymphocytes. For example, peripheral white cells are purified from a host and cultured with purified antigen. The presence or absence of one or factors indicating immunity are then detected. Other examples include assays that measure cell proliferation (lymphocyte proliferation or transformation assays) following exposure to purified antigen, and assays that measure cell death (including apoptosis) following exposure to purified antigen;
(iii) assays in which purified antibody specific for antigen is used to detect antigen in the host. For example, purified antibody is bound to solid phase, host tissue is then applied followed by another antibody specific for the antigen to be detected. There are many examples of this approach including ELISA, RIA;
(iv) assays in which a purified anti-idiotypic antibody is used to detect host antibody. For example, anti-idiotypic antibody is adsorbed to solid phase, host serum is added and anti-Fc antibody is added to bind to any host antibodies having been bound by the anti-idiotypic antibody.

The immunoassays can be applied in vitro or in vivo.

In one embodiment, the disease is typically a cancer such as carcinoma, sarcoma, lymphoma, or leukemia. Carcinomas that may be detected include, but not limited to, prostate, breast, skin, lung, cervix, uterus, stomach, oesophagus, bladder, and colon cancers.

Whilst any body fluid can be used to detect any of these diseases, some body fluids may be more appropriate than others to detect certain diseases, for example urine may be more appropriate to detect prostate cancer and blood for detecting blood cancers such as lymphoma.

In another embodiment there is provided a method for determining whether an individual has a cancer including the steps of:
    contacting a cell, a tissue or an extra-cellular body fluid with a peptide as described above in conditions for forming an immune complex between the peptide and an antibody in the cell, tissue or extra-cellular body fluid; or
    contacting a cell, tissue or extra cellular body fluid with an antibody or fragment thereof in conditions for forming an immune complex as described above, and
    detecting whether an immune complex has been formed, wherein detection of an immune complex determines that an individual has a cancer.

In a further embodiment there is provided use of anti purinergic (P2X) receptor antibody or fragment thereof as described above, or a peptide as described above for determining whether an individual has a cancer.

In certain embodiments, cancer is selected from the group consisting of prostate cancer, invasive breast cancer, melanoma, adenocarcinoma of the bowel, serous ovarian cancer, squamous cell cancer of the cervix, endometrial cancer, small cell lung cancer, hepatocellular carcinoma, transitional cell carcinoma of the bladder, gastrointestinal stromal tumour, endometrial stromal tumour, pituitary cancer, mesothelioma, Hodgkin's lymphoma and thyroid papillary.

In yet further embodiments there is provided a kit or composition for determining whether a cell, tissue or extra-cellular body fluid contains a non ATP-binding P2X7 receptor, monomer or fragment thereof, or an antibody against same including:
    a peptide as described above; and/or an antibody or fragment thereof as described above; and/or
    non ATP-binding P2X7 receptor, monomer or fragment thereof; and optionally
    a further antibody for binding to the peptide, antibody or fragment thereof or the non ATP-binding P2X7 receptor, monomer or fragment thereof;
    written instructions for use of the kit in a method described above.

Kits are provided which contain the necessary reagents to carry out the assays of the present invention. The kit may include one or more compartments, each to receive one or more containers such as: (a) a first container comprising one of the components of the present invention described above; and (b) one or more other containers comprising one or more of the following: wash reagents, reagents capable of detecting presence of the antibody or peptide.

The containers allow one to efficiently transfer reagents from one compartment to another compartment such that the samples and reagents are not cross-contaminated, and the agents or solutions of each container can be added in a quantitative fashion from one compartment to another.

The kit typically contains containers which may be formed from a variety of materials such as glass or plastic, and can include for example, bottles, vials, syringes, and test tubes. A label typically accompanies the kit, and includes any writing or recorded material, which may be electronic or computer readable form (e.g., disk, optical disc, or tape) providing instructions or other information for used of the contents of the kit. The label indicates that the formulation is used for diagnosing or treating the disorder of choice.

One skilled in the art will readily recognize that the disclosed antibodies and peptides of the present invention can be readily incorporated into one of the established kit formats which are well known in the art.

In other embodiments there is provided a pharmaceutical composition including an antibody or fragment thereof as described above, or a peptide as described above, together with a pharmaceutically acceptable carrier, diluent or excipient.

In the preparation of the pharmaceutical compositions comprising the antibodies or peptides described in the teachings herein, a variety of vehicles and excipients and routes of administration may be used, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of the antibodies or peptides, or mixture of antibodies or mixture of peptides, or suitable salts thereof.

The pharmaceutical composition may be formulated as powders, granules, solutions, suspensions, aerosols, solids, pills, tablets, capsules, gels, topical creams, suppositories, transdermal patches, and other formulations known in the art.

For the purposes described herein, pharmaceutically acceptable salts of the antibodies and peptides is intended to include any art recognized pharmaceutically acceptable salts including organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. Thus, the antibodies or peptides, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as solid formulations in appropriate excipients.

The pharmaceutical compositions will often further comprise one or more buffers (e.g., neutral buffered saline or phosphate buffered saline), carbohydrates (e.g., glucose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, adjuvants (e.g., aluminium hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

While any suitable carrier known to those of ordinary skill in the art may be employed in the compositions of this invention, the type of carrier will typically vary depending on the mode of administration. Antibody and peptide compositions may be formulated for any appropriate manner of administration, including for example, oral, nasal, mucosal, intravenous, intraperitoneal, intradermal, subcutaneous, and intramuscular administration.

For parenteral administration, the compositions can be administered as injectable dosages of a solution or suspension of the substance in a physiologically acceptable diluent with a pharmaceutical carrier that can be a sterile liquid such as sterile pyrogen free water, oils, saline, glycerol, polyethylene glycol or ethanol. Additionally, auxiliary substances, such as wetting or emulsifying agents, surfactants, pH buffering substances and the like can be present in compositions.

Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate. Antibodies and peptides can be administered in the form of a depot injection or implant preparation which can be formulated in such a manner as to permit a sustained release of the active ingredient. An exemplary composition comprises antibody at 5 mg/ml, formulated in aqueous buffer consisting of 50 mM L-histidine, 150 mM NaCl, adjusted to pH 6.0 with HCl.

Typically, the compositions are prepared as injectables, either as liquid solutions or suspensions; solid or powder forms suitable for reconstitution with suitable vehicles, including by way example and not limitation, sterile pyrogen free water, saline, buffered solutions, dextrose solution, etc., prior to injection. The preparation also can be emulsified or encapsulated in liposomes or micro particles such as polylactide, polyglycolide, or copolymers.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles, as indicated above.

Alternatively, a pharmaceutical composition may be stored in a freeze-dried condition requiring only the addition of a sterile liquid carrier immediately prior to use.

In related embodiments there is provided a method of treatment of a disease characterised by the expression of a non ATP-binding P2X7 receptor, monomer or fragment thereof including the step of providing an antibody or fragment thereof as described above, or a peptide as described above to an individual requiring said treatment.

Methods of immunotargeting cancer cells using antibodies or antibody fragments are well known in the art. U.S. Pat. No. 6,306,393 describes the use of anti-CD22 antibodies in the immunotherapy of B-cell malignancies, and U.S. Pat. No. 6,329,503 describes immunotargeting of cells that express serpentine transmembrane antigens. Antibodies described herein (including humanized or human monoclonal antibodies or fragments or other modifications thereof, optionally conjugated to cytotoxic agents) can be introduced into a patient such that the antibody binds to cancer cells and mediates the destruction of the cells and the tumor and/or inhibits the growth of the cells or the tumor.

Without intending to limit the disclosure, mechanisms by which such antibodies can exert a therapeutic effect may include complement-mediated cytolysis, antibody-dependent cellular cytotoxicity (ADCC)1 modulating the physiologic function of the tumor antigen, inhibiting binding or signal transduction pathways, modulating tumor cell differentiation, altering tumor angiogenesis factor profiles, modulating the secretion of immune stimulating or tumor suppressing cytokines and growth factors, modulating cellular adhesion, and/or by inducing apoptosis.

The antibodies can also be conjugated to toxic or therapeutic agents, such as radioligands or cytosolic toxins, and may also be used therapeutically to deliver the toxic or therapeutic agent directly to tumor cells.

By "treatment" herein is meant therapeutic or prophylactic treatment, or a suppressive measure for the disease, disorder or undesirable condition. Treatment encompasses administration of the subject antibodies in an appropriate form prior to the onset of disease symptoms and/or after clinical manifestations, or other manifestations, of the disease to reduce disease severity, halt disease progression, or eliminate the disease.

Prevention of the disease includes prolonging or delaying the onset of symptoms of the disorder or disease, preferably in a subject with increased susceptibility to the disease.

The therapeutic preparations can use nonmodified antibodies or antibodies conjugated with a therapeutic compound, such as a toxin or cytotoxic molecule; depending on the functionality of the antibody. Generally, when nonmodified antibodies are used, they will typically have a functional Fc region. By "functional Fc region" herein is meant a minimal sequence for effecting the biological function of Fc, such as binding to Fc receptors, particularly FcγR (e.g., FcγR1, RIIA, RIIB, RIIIA, RIIIB).

Without being bound by theory, it is believed that the Fc region may affect the effectiveness of anti ¬ tumor monoclonal antibodies by binding to Fc receptors immune effector cells and modulating cell mediated cytotoxicity, endocytosis, phagocytosis, release of inflammatory cytokines, complement mediate cytotoxicity, and antigen presentation. In this regard, polyclonal antibodies, or mixtures of monoclonals will be advantageous because they will bind to different epitopes and thus have a higher density of Fc on the cell surface as compared to when a single monoclonal antibody is used. Of course, to enhance their effectiveness in depleting targeted cells, or where nonmodified antibodies are not therapeutically effective, antibodies conjugated to toxins or cytotoxic agents may be used.

The antibody compositions may be used either alone or in combination with other therapeutic agents to increase efficacy of traditional treatments or to target abnormal cells not targeted by the antibodies. Combining the antibody therapy method with a chemotherapeutic, radiation or surgical regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well. Furthermore, treatment of cancer patients with the antibody with tumors resistant to chemotherapeutic agents might induce sensitivity and responsiveness to these agents in combination.

In one aspect, the antibodies are used adjunctively with therapeutic cytotoxic agents, including, by way of example and not limitation, busulfan, thioguanine, idarubicin, cytosine arabinoside, 6-mercaptopurine, doxorubicin, daunorubicin, etoposide, and hydroxyurea. Other agents useful as adjuncts to antibody therapy are compounds directed specifically to the abnormal cellular molecule found in the disease state. These agents will be disease specific. For example, for treating chronic myeloid leukemia arising from BCR-ABL activity, one class of useful compounds are inhibitors of abl kinase activity, such as Imatinib, an inhibitor of bcr-abl kinase, and antisense oligonucleotides against bcr (e.g., Oblimersen). Other agents include, among others, interferon-alpha, humanized anti-CD52, deacetylase inhibitor FR901228 (depsipeptide), and the like.

The amount of the compositions needed for achieving a therapeutic effect will be determined empirically in accordance with conventional procedures for the particular purpose. Generally, for administering the compositions ex vivo or in vivo for therapeutic purposes, the compositions are given at a pharmacologically effective dose. By "pharmacologically effective amount" or "pharmacologically effective dose" is an amount sufficient to produce the desired physiological effect or amount capable of achieving the desired result, particularly for treating or retreating the disorder or disease condition, including reducing or eliminating one or more symptoms or manifestations of the disorder or disease.

As an illustration, administration of antibodies to a patient suffering from prostate cancer provides a therapeutic benefit not only when the underlying disease is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

The amount administered to the host will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but is not limited to, size and weight of the subject, the age and sex of the subject, the severity of the symptom, the stage of the disease, method of delivery of the agent, half-life of the agents, and efficacy of the agents. Stage of the disease to consider includes whether the disease is acute or chronic, relapsing or remitting phase, and the progressiveness of the disease. Determining the dosages and times of administration for a therapeutically effective amount are well within the skill of the ordinary person in the art.

For any compositions of the present disclosure, the therapeutically effective dose is readily determined by methods well known in the art. For example, an initial effective dose can be estimated from cell culture or other in vitro assays. For example, Sliwkowsky, M X et al., Semin. Oncol. 26.suppl. 12) 60-70 (1999) describes in vitro measurements of antibody dependent cellular cytotoxicity. A dose can then be formulated in animal models to generate a circulating concentration or tissue concentration, including that of the IC50 as determined by the cell culture assays.

In addition, the toxicity and therapeutic efficacy are generally determined by cell culture assays and/or experimental animals, typically by determining a LD50 (lethal dose to 50% of the test population) and ED50 (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein. Guidance is also found in standard reference works, for example Fingl and Woodbury, General Principles In: The Pharmaceutical Basis of Therapeutics pp. 1-46 (1975), and the references cited therein.

To achieve an initial tolerizing dose, consideration is given to the possibility that the antibodies may be immunogenic in humans and in non-human primates. The immune response may be biologically significant and may impair the therapeutic efficacy of the antibody even if the antibody is partly or chiefly comprised of human immunoglobulin sequences such as, for example, in the case of a chimeric or humanized antibody.

Within certain embodiments, an initial high dose of antibody is administered such that a degree of immunological tolerance to the therapeutic antibody is established.

The tolerizing dose is sufficient to prevent or reduce the induction of an antibody response to repeat administration of the committed progenitor cell specific antibody.

Preferred ranges for the tolerizing dose are between 10 mg/kg body weight to 50 mg/kg body weight, inclusive. More preferred ranges for the tolerizing dose are between 20 and 40 mg/kg, inclusive. Still more preferred ranges for the tolerizing dose are between 20 and 25 mg/kg, inclusive.

Within these therapeutic regimens, the therapeutically effective dose of antibodies is preferably administered in the range of 0.1 to 10 mg/kg body weight, inclusive. More preferred second therapeutically effective doses are in the range of 0.2 to 5 mg/kg body weight, inclusive. Still more preferred therapeutically effective doses are in the range of 0.5 to 2 mg/kg, inclusive. Within alternative embodiments, the subsequent therapeutic dose or doses may be in the same or different formulation as the tolerizing dose and/or may be administered by the same or different route as the tolerizing dose.

For the purposes of this invention, the methods of administration are chosen depending on the condition being treated, the form of the subject antibodies, and the pharmaceutical composition.

Administration of the antibody compositions can be done in a variety of ways, including, but not limited to, continuously, subcutaneously, intravenously, orally, topically, transdermal, intraperitoneal, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, intraperitoneal administration can be accompanied by intravenous injections. Preferably the therapeutic doses are administered intravenously, intraperitonealy, intramuscularly, or subcutaneously.

The compositions may be administered once or several times. In some embodiments, the compositions may be administered once per day, a few or several times per day, or even multiple times per day, depending upon, among other things, the indication being treated and the judgement of the prescribing physician.

Administration of the compositions may also be achieved through sustained release or long-term delivery methods, which are well known to those skilled in the art. By "sustained release or" "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the antibodies, such as biodegradable polymers described above; pumps, including peristaltic pumps and fluorocarbon propellant pumps; osmotic and mini-osmotic pumps; and the like.

The method of the invention contemplates the administration of single monoclonal antibodies and any antibody that recognizes the particular antigens recognized by these antibodies, as well as combinations, of different mAbs. Two or more monoclonal antibodies may provide an improved effect compared to a single antibody. Alternatively, a combination of an antibody with an antibody that binds a different antigen may provide an improved effect compared to a single antibody. Such mAb cocktails may have certain advantages inasmuch as they contain mAbs, which exploit different effector mechanisms or combine directly cytotoxic mAbs with mAbs that rely on immune effector functionality. Such mAbs in combination may exhibit synergistic therapeutic effects.

It will be understood that the invention disclosed and defined in this specification extends to all alternative combinations of two or more of the individual features mentioned or evident from the text or drawings. All of these different combinations constitute various alternative aspects of the invention.

The following protocols are provided as non-limiting examples for the purpose of illustrating the invention.

EXAMPLES

Example 1

Anti-nonfunctional $P2X_7$ antibody was raised against the peptide KYYKENNVEKRTLIKVF (SEQ ID NO: 2) or Lys-Tyr-Tyr-Lys-Glu-Asn-Asn-Val-Glu-Lys-Arg-Thr-Leu-Ile-Lys-Val-Phe, representing amino acids 297-313 of the human $P2X_7$ protein of SEQ ID NO: 1. The peptide was synthesized by solid phase chemistry (Mimotopes Pty Ltd, Melbourne, Australia) to high purity (>95%) as judged by mass spectroscopy. A C-terminal Cys (C) residue was attached to the sequence and to this was attached the cross-linker MCS (6-Maleimido-Caproic Acid N-Hydroxysuccinimide Ester) for conjugating the peptide to carrier proteins including separately Diphtheria toxoid, bovine serum albumin and ovalbumin by Mimotopes.

Example 2

Female New Zealand White rabbits, aged between 10-12 weeks, were immunized according to the following schedule.

On day one, each rabbit received 200 ug of $P2X_7$ epitope conjugated to diphtheria toxoid (total antigen weight ~500 ug of conjugated epitope). This conjugated peptide was supplied by Mimotopes Pty Ltd as a stable solution.

The epitope conjugate was diluted in sterile PBS to a concentration of 500 ug per 0.8 ml PBS. To this was added 0.1 ml of DEAE/Dextran/QUILA™ solution (2.5 mg QUILA™ plus 25 mg DEAE/Dextran per mL of PBS) and 1.2 mL of Montanide 15A50V. This solution was emulsified using glass luerloc syringes and a narrow bore luerloc coupling.

Animals were each injected with 2 ml of the epitope adjuvant emulsion at multiple subcutaneous and intra-muscular sites.

The above was repeated at 6-weeks and 9-weeks post initial injections. At week 10, the rabbits were injected intravenously with 1 ml of sterile PBS containing 50 ug of DT-conjugated $P2X_7$ epitope. Four days later, the rabbits were bled out and the serum containing the antibody was stored for future analysis and use in immunoassays.

Example 3

The procedure in Example 2 was used except that mice were injected with 20 ug of $P2X_7$ epitope (~50 ug of DT-conjugate) in 0.2 mL of epitope adjuvant emulsion.

Four days after the intravenous injection, antibody titers were measured in mouse blood and the highest titer mice were selected as spleen donors for hybridoma fusions.

Example 4

Mice selected above were used as spleen cell donors and these cells were fused with mouse SP20 myeloma cells to form hybridoma cell lines according to the 96-well plate format modification of the original protocol described by Kohler and Milstein.

Cell lines were selected for stability and production of the specific antibody to particular $P2X_7$ epitopes.

Example 5

A monoclonal antibody with suitably high affinity for the target epitope was selected for the IHC study. The binding characteristics of the antibody was tested by measuring the interaction with the target epitope on a Biacore instrument. A total of 550 resonance units of binding was achieved in the 60 second loading time showing slow on rate. A very slow off rate was apparent following cessation of loading with no measurable diminution of binding over the subsequent 10 minutes.

Example 6

Binding of the monoclonal antibody to fixed and permeabilized C11STH cells expressing the non-functional receptor was performed on a flow cytometer (Becton-Dickenson) using Alexa-488 label. The mean value was 90.8 compared with negative controls of 1.9. Binding of the monoclonal antibody to receptors on the surface of unfixed live cells was also assessed. The mean value was 5.8 compared with 0.34 for the negative control.

Example 7

For fixed cells, standard fluorescent antibody staining and confocal microscopy was used as follows. Fixed cells on poly-L-lysine-coated glass coverslips in 48-well plates were incubated with 20% normal horse serum in phosphate buffered saline pH7.5 (PBS) for 20 minutes, washed with PBS for 5 minutes then incubated with primary antibody for 30 min, washed with PBS for 5 minutes and finally labeled with fluorescent labeled secondary antibody (Jackson Immunologics) for 30 minutes. Cells were then washed twice (2×5 minutes) with PBS before mounting the coverslips on slides in 50% glycerol in PBS. Cells were visualized with a Leica TCS NT UV laser confocal microscope system with the pinhole set at 1.0. Murine isotype control antibodies were used routinely as negative controls and showed no staining. Western blots of HEK293 cells transfected with P2X7 revealed a single band at approximately 75 kDa that was absent in non-transfected cells and in samples of homogenates pre-treated with the epitope. Cell protein extracts (30 ug) together with molecular weight markers were fractionated on sodium dodecyl sulfate polyacrylamide gel (8-16%) (Novex). Proteins were electro-blotted on Immobilon-P membrane (Millipore). Western blots were developed using the ECL-chemiluminescence system (Amersham).

Example 8

A total of 25 different cases of breast cancers, 25 cases of skin cancers and 25 cases of prostate cancers were examined by immunohistochemistry. There was no cross-reactivity between the functional receptors present on the red blood cells and the non-functional receptor antibody (data not shown).

Examples of cancer tissue including prostate cancer, breast cancer as represented by ductal carcinoma in situ and melanoma all stained for non-functional $P2X_7$. The epithelium in normal tissues with no adjacent tumour was devoid of the receptor while all cancer cases stained for the receptor.

Cancer cell lines derived from these and other tissues an other were similarly found to express the receptors. Examples tested and found positive include ADDP, PC3, LNCap, MCF7, MDA-MB-235, MDA-MB-431, NCIH460, NCIH69, NCIH596, DU145, ACHN, 786-O, Hep3B2, C11STH and BT474. Similar patterns of expression were seen on tumor xenografts of ovarian ADDP and lung NCIH69 respectively. The non-functional $P2X_7$ receptors were found on the plasma membrane with correspondingly little residual cytoplasmic receptor in the most advanced stages of the cancers. In contrast, lower grade tumours exhibited a preponderance of cells in which a large proportion of the receptors remain intracellular. Such a progressive transport of non-functioning apoptotic receptors to the plasma membrane over the course of the disease progression indicates that cancer cell lines should exhibit non-functional $P2X_7$ receptors on the plasma membrane rather than being largely intracellular.

Normal epithelial tissue is devoid of the non-functional receptors while cancer tissues are all labelled. Different breast cancers, including both invasive and in situ lobular and ductal carcinomas were examined. All types expressed non-functional receptors. Epithelial cells in these and other normal, non-cancerous tissues such as bowel, bladder, ovarian, uterine, cervical, stomach and lung were found to be devoid of non-functional receptors.

Areas of morphologically normal tissue surrounding tumours in prostate also expressed the receptors consistent with the field-effect in which tumour cells influence surrounding normal epithelium in connected ducts thereby alerting these cells to the presence of a developing tumour. In response, these cells begin deploying receptor, initially in an entirely intracellular location but eventually on the plasma membrane.

In addition to the breast, skin and prostate cancer samples, other examples of epithelial cell cancers, all of which expressed non-functional $P2X_7$ included bowel adenocarcinoma, invasive ovarian cancer, squamous cell carcinoma of the cervix, endometrial carcinoma of the uterus, small cell lung cancer, hepatocellular carcinoma, transitional cell carcinoma of the bladder and Barrett's mucosa with adenocarcinoma.

Human cancers of non-epithelial cell origin were also examined. All were found to express the non-functional P2X$_7$ receptors. Examples of mesenchymal cancers include gastrointestinal stromal tumour and endometrial stromal tumour. Equally, other tumours derived from this cell type such as Ewing's sarcoma express the receptors as do brain tumours such as oligodendrogliomas and astrocytomas, as do pituitary carcinoma. Mesothelioma, a cancer derived from pleural cells, also express non functional receptors, as do solid tumours derived from blood cells such as mantle cell lymphomas. Hodgkin's lymphoma and thyroid papillary are examples.

Cross-reactivity between human and other mammalian cancers such as prostate, breast and skin from dogs and cats and melanoma in mice was observed using the same antibody to human receptor. These observations add weight to the conclusion that the cancer cell target is ubiquitous.

Example 9

There are indications that the receptor expression alters with tumour grade providing the potential to differentiate between latent and aggressive forms of cancer. Certainly, very slow growing low grade prostate cancers exhibit a pattern of receptor expression that is almost entirely intracellular, while cases of invasive prostate cancer exhibit more plasma membrane and myoepithelial cell labelling together with a significantly elevated receptor density.

Low grade and clinically unimportant prostate cancer can be differentiated from clinically important prostate cancer by the appearance of the surrounding areas of normal epithelium. Clinically important cancers include those that are likely to spread into the prostatic stroma and metastasize. Direct sampling of the tumour with trans rectal ultrasound (TRUS) guided needle biopsies may detect a clinically significant tumour, thus making diagnosis straightforward. In cases in which the extant tumour is sampled in a region that is lower grade (eg Gleason 3+3) with other areas (eg Gleason 3+4) missed, staining for the non-functional P2X$_7$ receptor shows that areas of normal morphology also sampled in the prostate show intense levels of receptor expression and myoepithelial stain, indicating the presence of tissue that is metastasizing. Even cases in which the tumour is completely missed, such as tumours confined to the apical lobe out of reach of the needles, the presence and status of the tumour is readily detected as the field-effect emanating from the tumour to surrounding epithelium alerts the pathologist to the presence of the tumour and the likely grade.

Example 10

Dysplastic tissue is difficult to diagnose and conditions such as Barrett's mucosa with dysplasia need to be monitored given the propensity of the tissue to transform to adenocarcinoma. The differentiation between dysplastic tissue that will remain benign and tissue that is at extreme risk of imminent transformation again centres on the presence of associated myoepithelial stain showing a dramatic up-regulation of non-functional P2X$_7$ receptor expression. Similar results were observed for other dysplastic bowel conditions such as colitis. In tissue samples of Barrett's with dysplasia there was no staining indicating a benign condition while samples with intense myoepithelial stain identified a subject that had an associated adenocarcinoma.

Early cases of neoplastic transformation including cervical intraepithelial neoplasia (CIN) grades 1-3 also showed increased levels of receptor expression and cases such as ovarian serous borderline were categorised as being benign (unstained) and those that were going to transform (heavy epithelial stain).

The above results indicate that an epitope that includes one or more amino acids of the sequence KYYKENNVEKRTLIKVF (SEQ ID NO:2) has expression on a broad selection of epithelial cancer tissues and cells.

The invention claimed is:

1. A purified antibody that binds to a peptide consisting of the amino acid sequence shown in SEQ ID NO: 3.

2. A pharmaceutical composition including an antibody according to claim 1, together with a pharmaceutically acceptable carrier, diluent or excipient.

3. The antibody according to claim 1, wherein the antibody is monoclonal.

4. The antibody according to claim 1, wherein the antibody is polyclonal.

5. The antibody according to claim 1, wherein the antibody is selected from the group consisting of dAb, Fab, Fd, Fv, F(ab')2 and scFv.

6. A pharmaceutical composition including the antibody according to claim 5, together with a pharmaceutically acceptable carrier, diluent or excipient.

7. A purified antibody that binds to an epitope on a P2X7 receptor, the epitope consisting of the amino acid sequence shown in SEQ ID NO: 3.

8. An antibody according to claim 7, wherein the antibody binds to an epitope within SEQ ID NO: 2.

9. The antibody according to claim 7, wherein the antibody is monoclonal.

10. The antibody according to claim 7, wherein the antibody is polyclonal.

11. The antibody according to claim 7, wherein the antibody is selected from the group consisting of dAb, Fab, Fd, Fv, F(ab')2 and scFv.

12. A pharmaceutical composition including the antibody according to claim 11, together with a pharmaceutically acceptable carrier, diluent or excipient.

13. A pharmaceutical composition including the antibody according to claim 7, together with a pharmaceutically acceptable carrier, diluent or excipient.

* * * * *

SEQUENCE LISTING

<160> NUMBER OF SEQ ID NOS: 12

<210> SEQ ID NO 1
<211> LENGTH: 595
<212> TYPE: PRT
<213> ORGANISM: Homo sapiens

<400> SEQUENCE: 1

```
Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95
```

-continued

```
Leu Gln Gly Asn Ser Phe Phe Val Met Thr Asn Phe Leu Lys Thr Glu
            100                 105                 110
Gly Gln Glu Gln Arg Leu Cys Pro Glu Tyr Pro Thr Arg Thr Leu
        115                 120                 125
Cys Ser Ser Asp Arg Gly Cys Lys Lys Gly Trp Met Asp Pro Gln Ser
130                 135                 140
Lys Gly Ile Gln Thr Gly Arg Cys Val Val His Glu Gly Asn Gln Lys
145                 150                 155                 160
Thr Cys Glu Val Ser Ala Trp Cys Pro Ile Glu Ala Val Glu Glu Ala
                165                 170                 175
Pro Arg Pro Ala Leu Leu Asn Ser Ala Glu Asn Phe Thr Val Leu Ile
            180                 185                 190
Lys Asn Asn Ile Asp Phe Pro Gly His Asn Tyr Thr Thr Arg Asn Ile
        195                 200                 205
Leu Pro Gly Leu Asn Ile Thr Cys Thr Phe His Lys Thr Gln Asn Pro
    210                 215                 220
Gln Cys Pro Ile Phe Arg Leu Gly Asp Ile Phe Arg Glu Thr Gly Asp
225                 230                 235                 240
Asn Phe Ser Asp Val Ala Ile Gln Gly Gly Ile Met Gly Ile Glu Ile
                245                 250                 255
Tyr Trp Asp Cys Asn Leu Asp Arg Trp Phe His His Cys Arg Pro Lys
            260                 265                 270
Tyr Ser Phe Arg Arg Leu Asp Asp Lys Thr Thr Asn Val Ser Leu Tyr
        275                 280                 285
Pro Gly Tyr Asn Phe Arg Tyr Ala Lys Tyr Tyr Lys Glu Asn Asn Val
    290                 295                 300
Glu Lys Arg Thr Leu Ile Lys Val Phe Gly Ile Arg Phe Asp Ile Leu
305                 310                 315                 320
Val Phe Gly Thr Gly Gly Lys Phe Asp Ile Ile Gln Leu Val Val Tyr
                325                 330                 335
Ile Gly Ser Thr Leu Ser Tyr Phe Gly Leu Ala Ala Val Phe Ile Asp
            340                 345                 350
Phe Leu Ile Asp Thr Tyr Ser Ser Asn Cys Cys Arg Ser His Ile Tyr
        355                 360                 365
Pro Trp Cys Lys Cys Cys Gln Pro Cys Val Val Asn Glu Tyr Tyr Tyr
    370                 375                 380
Arg Lys Lys Cys Glu Ser Ile Val Glu Pro Lys Pro Thr Leu Lys Tyr
385                 390                 395                 400
Val Ser Phe Val Asp Glu Ser His Ile Arg Met Val Asn Gln Gln Leu
                405                 410                 415
Leu Gly Arg Ser Leu Gln Asp Val Lys Gly Gln Glu Val Pro Arg Pro
            420                 425                 430
Ala Met Asp Phe Thr Asp Leu Ser Arg Leu Pro Leu Ala Leu His Asp
        435                 440                 445
Thr Pro Pro Ile Pro Gly Gln Pro Glu Glu Ile Gln Leu Leu Arg Lys
    450                 455                 460
Glu Ala Thr Pro Arg Ser Arg Asp Ser Pro Val Trp Cys Gln Cys Gly
465                 470                 475                 480
Ser Cys Leu Pro Ser Gln Leu Pro Glu Ser His Arg Cys Leu Glu Glu
                485                 490                 495
Leu Cys Cys Arg Lys Lys Pro Gly Ala Cys Ile Thr Thr Ser Glu Leu
            500                 505                 510
Phe Arg Lys Leu Val Leu Ser Arg His Val Leu Gln Phe Leu Leu Leu
        515                 520                 525
```

```
Tyr Gln Glu Pro Leu Leu Ala Leu Asp Val Asp Ser Thr Asn Ser Arg
        530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
            565                 570                 575

Ile Arg Lys Glu Phe Pro Lys Ser Glu Gly Gln Tyr Ser Gly Phe Lys
        580                 585                 590

Ser Pro Tyr
        595

<210> SEQ ID NO 2
<211> LENGTH: 17
<212> TYPE: PRT
<213> ORGANISM: Homo sapiens

<400> SEQUENCE: 2

Lys Tyr Tyr Lys Glu Asn Asn Val Glu Lys Arg Thr Leu Ile Lys Val
1               5                   10                  15

Phe

<210> SEQ ID NO 3
<211> LENGTH: 49
<212> TYPE: PRT
<213> ORGANISM: Homo sapiens

<400> SEQUENCE: 3

Lys Thr Thr Asn Val Ser Leu Tyr Pro Gly Tyr Asn Phe Arg Tyr Ala
1               5                   10                  15

Lys Tyr Tyr Lys Glu Asn Asn Val Glu Lys Arg Thr Leu Ile Lys Val
            20                  25                  30

Phe Gly Ile Arg Phe Asp Ile Leu Val Phe Gly Thr Gly Gly Lys Phe
        35                  40                  45

Asp

<210> SEQ ID NO 4
<211> LENGTH: 505
<212> TYPE: PRT
<213> ORGANISM: Homo sapiens

<400> SEQUENCE: 4

Met Thr Pro Gly Asp His Ser Trp Gly Asn Ser Phe Phe Val Met Thr
1               5                   10                  15

Asn Phe Leu Lys Thr Glu Gly Gln Gln Arg Leu Cys Pro Glu Tyr
            20                  25                  30

Pro Thr Arg Arg Thr Leu Cys Ser Ser Asp Arg Gly Cys Lys Lys Gly
        35                  40                  45

Trp Met Asp Pro Gln Ser Lys Gly Ile Gln Thr Gly Arg Cys Val Val
        50                  55                  60

His Glu Gly Asn Gln Lys Thr Cys Glu Val Ser Ala Trp Cys Pro Ile
65                  70                  75                  80

Glu Ala Val Glu Glu Ala Pro Arg Pro Ala Leu Leu Asn Ser Ala Glu
                85                  90                  95

Asn Phe Thr Val Leu Ile Lys Asn Asn Ile Asp Phe Pro Gly His Asn
            100                 105                 110

Tyr Thr Thr Arg Asn Ile Leu Pro Gly Leu Asn Ile Thr Cys Thr Phe
        115                 120                 125
```

His Lys Thr Gln Asn Pro Gln Cys Pro Ile Phe Arg Leu Gly Asp Ile
130                 135                 140

Phe Arg Glu Thr Gly Asp Asn Phe Ser Asp Val Ala Ile Gln Gly Gly
145                 150                 155                 160

Ile Met Gly Ile Glu Ile Tyr Trp Asp Cys Asn Leu Asp Arg Trp Phe
                165                 170                 175

His His Cys Arg Pro Lys Tyr Ser Phe Arg Arg Leu Asp Asp Lys Thr
            180                 185                 190

Thr Asn Val Ser Leu Tyr Pro Gly Tyr Asn Phe Arg Tyr Ala Lys Tyr
        195                 200                 205

Tyr Lys Glu Asn Asn Val Glu Lys Arg Thr Leu Ile Lys Val Phe Gly
210                 215                 220

Ile Arg Phe Asp Ile Leu Val Phe Gly Thr Gly Gly Lys Phe Asp Ile
225                 230                 235                 240

Ile Gln Leu Val Val Tyr Ile Gly Ser Thr Leu Ser Tyr Phe Gly Leu
                245                 250                 255

Ala Ala Val Phe Ile Asp Phe Leu Ile Asp Thr Tyr Ser Ser Asn Cys
            260                 265                 270

Cys Arg Ser His Ile Tyr Pro Trp Cys Lys Cys Gln Pro Cys Val
        275                 280                 285

Val Asn Glu Tyr Tyr Arg Lys Lys Cys Glu Ser Ile Val Glu Pro
290                 295                 300

Lys Pro Thr Leu Lys Tyr Val Ser Phe Val Asp Glu Ser His Ile Arg
305                 310                 315                 320

Met Val Asn Gln Gln Leu Leu Gly Arg Ser Leu Gln Asp Val Lys Gly
                325                 330                 335

Gln Glu Val Pro Arg Pro Ala Met Asp Phe Thr Asp Leu Ser Arg Leu
            340                 345                 350

Pro Leu Ala Leu His Asp Thr Pro Ile Pro Gly Gln Pro Glu Glu
        355                 360                 365

Ile Gln Leu Leu Arg Lys Glu Ala Thr Pro Arg Ser Arg Asp Ser Pro
370                 375                 380

Val Trp Cys Gln Cys Gly Ser Cys Leu Pro Ser Gln Leu Pro Glu Ser
385                 390                 395                 400

His Arg Cys Leu Glu Glu Leu Cys Cys Arg Lys Lys Pro Gly Ala Cys
                405                 410                 415

Ile Thr Thr Ser Glu Leu Phe Arg Lys Leu Val Leu Ser Arg His Val
            420                 425                 430

Leu Gln Phe Leu Leu Leu Tyr Gln Glu Pro Leu Leu Ala Leu Asp Val
        435                 440                 445

Asp Ser Thr Asn Ser Arg Leu Arg His Cys Ala Tyr Arg Cys Tyr Ala
450                 455                 460

Thr Trp Arg Phe Gly Ser Gln Asp Met Ala Asp Phe Ala Ile Leu Pro
465                 470                 475                 480

Ser Cys Cys Arg Trp Arg Ile Arg Lys Glu Phe Pro Lys Ser Glu Gly
                485                 490                 495

Gln Tyr Ser Gly Phe Lys Ser Pro Tyr
            500                 505

<210> SEQ ID NO 5
<211> LENGTH: 425
<212> TYPE: PRT
<213> ORGANISM: Homo sapiens

<400> SEQUENCE: 5

-continued

```
Met Asp Gly Pro Ala Glu Gln Arg Pro Ala Leu Leu Asn Ser Ala Glu
1               5                   10                  15

Asn Phe Thr Val Leu Ile Lys Asn Ile Asp Phe Pro Gly His Asn
            20                  25                  30

Tyr Thr Thr Arg Asn Ile Leu Pro Gly Leu Asn Ile Thr Cys Thr Phe
            35                  40                  45

His Lys Thr Gln Asn Pro Gln Cys Pro Ile Phe Arg Leu Gly Asp Ile
        50                  55                  60

Phe Arg Glu Thr Gly Asp Asn Phe Ser Asp Val Ala Ile Gln Gly Gly
65                  70                  75                  80

Ile Met Gly Ile Glu Ile Tyr Trp Asp Cys Asn Leu Asp Arg Trp Phe
                85                  90                  95

His His Cys Arg Pro Lys Tyr Ser Phe Arg Arg Leu Asp Asp Lys Thr
            100                 105                 110

Thr Asn Val Ser Leu Tyr Pro Gly Tyr Asn Phe Arg Tyr Ala Lys Tyr
            115                 120                 125

Tyr Lys Glu Asn Asn Val Glu Lys Arg Thr Leu Ile Lys Val Phe Gly
        130                 135                 140

Ile Arg Phe Asp Ile Leu Val Phe Gly Thr Gly Gly Lys Phe Asp Ile
145                 150                 155                 160

Ile Gln Leu Val Val Tyr Ile Gly Ser Thr Leu Ser Tyr Phe Gly Leu
                165                 170                 175

Ala Ala Val Phe Ile Asp Phe Leu Ile Asp Thr Tyr Ser Ser Asn Cys
            180                 185                 190

Cys Arg Ser His Ile Tyr Pro Trp Cys Lys Cys Gln Pro Cys Val
            195                 200                 205

Val Asn Glu Tyr Tyr Arg Lys Lys Cys Glu Ser Ile Val Glu Pro
210                 215                 220

Lys Pro Thr Leu Lys Tyr Val Ser Phe Val Asp Glu Ser His Ile Arg
225                 230                 235                 240

Met Val Asn Gln Gln Leu Leu Gly Arg Ser Leu Gln Asp Val Lys Gly
            245                 250                 255

Gln Glu Val Pro Arg Pro Ala Met Asp Phe Thr Asp Leu Ser Arg Leu
            260                 265                 270

Pro Leu Ala Leu His Asp Thr Pro Ile Pro Gly Gln Pro Glu Glu
            275                 280                 285

Ile Gln Leu Leu Arg Lys Glu Ala Thr Pro Arg Ser Arg Asp Ser Pro
            290                 295                 300

Val Trp Cys Gln Cys Gly Ser Cys Leu Pro Gln Leu Pro Glu Ser
305                 310                 315                 320

His Arg Cys Leu Glu Glu Leu Cys Cys Arg Lys Lys Pro Gly Ala Cys
            325                 330                 335

Ile Thr Thr Ser Glu Leu Phe Arg Lys Leu Val Leu Ser Arg His Val
            340                 345                 350

Leu Gln Phe Leu Leu Leu Tyr Gln Glu Pro Leu Leu Ala Leu Asp Val
            355                 360                 365

Asp Ser Thr Asn Ser Arg Leu Arg His Cys Ala Tyr Arg Cys Tyr Ala
            370                 375                 380

Thr Trp Arg Phe Gly Ser Gln Asp Met Ala Asp Phe Ala Ile Leu Pro
385                 390                 395                 400

Ser Cys Cys Arg Trp Arg Ile Arg Lys Glu Phe Pro Lys Ser Glu Gly
                405                 410                 415

Gln Tyr Ser Gly Phe Lys Ser Pro Tyr
            420                 425
```

<210> SEQ ID NO 6
<211> LENGTH: 354
<212> TYPE: PRT
<213> ORGANISM: Homo sapiens

<400> SEQUENCE: 6

```
Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Val Arg Asp Ser Glu Gly
            340                 345                 350

Ser Asp
```

<210> SEQ ID NO 7
<211> LENGTH: 306

<212> TYPE: PRT
<213> ORGANISM: Homo sapiens

<400> SEQUENCE: 7

Met Trp Gln Phe Arg Tyr Ala Lys Tyr Tyr Lys Glu Asn Asn Val Glu
1               5                   10                  15

Lys Arg Thr Leu Ile Lys Val Phe Gly Ile Arg Phe Asp Ile Leu Val
            20                  25                  30

Phe Gly Thr Gly Gly Lys Phe Asp Ile Ile Gln Leu Val Val Tyr Ile
        35                  40                  45

Gly Ser Thr Leu Ser Tyr Phe Gly Leu Ala Ala Val Phe Ile Asp Phe
    50                  55                  60

Leu Ile Asp Thr Tyr Ser Ser Asn Cys Cys Arg Ser His Ile Tyr Pro
65                  70                  75                  80

Trp Cys Lys Cys Cys Gln Pro Cys Val Val Asn Glu Tyr Tyr Tyr Arg
                85                  90                  95

Lys Lys Cys Glu Ser Ile Val Glu Pro Lys Pro Thr Leu Lys Tyr Val
            100                 105                 110

Ser Phe Val Asp Glu Ser His Ile Arg Met Val Asn Gln Gln Leu Leu
        115                 120                 125

Gly Arg Ser Leu Gln Asp Val Lys Gly Gln Glu Val Pro Arg Pro Ala
    130                 135                 140

Met Asp Phe Thr Asp Leu Ser Arg Leu Pro Leu Ala Leu His Asp Thr
145                 150                 155                 160

Pro Pro Ile Pro Gly Gln Pro Glu Glu Ile Gln Leu Leu Arg Lys Glu
                165                 170                 175

Ala Thr Pro Arg Ser Arg Asp Ser Pro Val Trp Cys Gln Cys Gly Ser
            180                 185                 190

Cys Leu Pro Ser Gln Leu Pro Glu Ser His Arg Cys Leu Glu Glu Leu
        195                 200                 205

Cys Cys Arg Lys Lys Pro Gly Ala Cys Ile Thr Thr Ser Glu Leu Phe
    210                 215                 220

Arg Lys Leu Val Leu Ser Arg His Val Leu Gln Phe Leu Leu Leu Tyr
225                 230                 235                 240

Gln Glu Pro Leu Leu Ala Leu Asp Val Asp Ser Thr Asn Ser Arg Leu
                245                 250                 255

Arg His Cys Ala Tyr Arg Cys Tyr Ala Thr Trp Arg Phe Gly Ser Gln
            260                 265                 270

Asp Met Ala Asp Phe Ala Ile Leu Pro Ser Cys Cys Arg Trp Arg Ile
        275                 280                 285

Arg Lys Glu Phe Pro Lys Ser Glu Gly Gln Tyr Ser Gly Phe Lys Ser
    290                 295                 300

Pro Tyr
305

<210> SEQ ID NO 8
<211> LENGTH: 275
<212> TYPE: PRT
<213> ORGANISM: Homo sapiens

<400> SEQUENCE: 8

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

```
Phe His Val Ile Ile Phe Ser Tyr Val Cys Phe Ala Leu Val Ser Asp
        35                  40                  45

Lys Leu Tyr Gln Arg Lys Glu Pro Val Ile Ser Val His Thr Lys
    50                  55                  60

Val Lys Gly Ile Ala Glu Val Lys Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
                100                 105                 110

Gly Gln Glu Gln Arg Leu Cys Pro Glu Tyr Pro Thr Arg Thr Leu
                115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
                180                 185                 190

Lys Asn Asn Ile Asp Phe Pro Gly His Asn Tyr Thr Thr Tyr Ala Lys
            195                 200                 205

Tyr Tyr Lys Glu Asn Asn Val Glu Lys Arg Thr Leu Ile Lys Val Phe
        210                 215                 220

Gly Ile Arg Phe Asp Ile Leu Val Phe Gly Thr Gly Gly Lys Phe Asp
225                 230                 235                 240

Ile Ile Gln Leu Val Val Tyr Ile Gly Ser Thr Leu Ser Tyr Phe Gly
                245                 250                 255

Leu Val Arg Asp Ser Leu Phe His Ala Leu Gly Lys Trp Phe Gly Glu
                260                 265                 270

Gly Ser Asp
275

<210> SEQ ID NO 9
<211> LENGTH: 274
<212> TYPE: PRT
<213> ORGANISM: Homo sapiens

<400> SEQUENCE: 9

Met Thr Pro Gly Asp His Ser Trp Gly Asn Ser Phe Phe Val Met Thr
1               5                   10                  15

Asn Phe Leu Lys Thr Glu Gly Gln Glu Gln Arg Leu Cys Pro Glu Tyr
                20                  25                  30

Pro Thr Arg Arg Thr Leu Cys Ser Ser Asp Arg Gly Cys Lys Lys Gly
            35                  40                  45

Trp Met Asp Pro Gln Ser Lys Gly Ile Gln Thr Gly Arg Cys Val Val
        50                  55                  60

His Glu Gly Asn Gln Lys Thr Cys Glu Val Ser Ala Trp Cys Pro Ile
65                  70                  75                  80

Glu Ala Val Glu Glu Ala Pro Arg Pro Ala Leu Leu Asn Ser Ala Glu
                85                  90                  95

Asn Phe Thr Val Leu Ile Lys Asn Asn Ile Asp Phe Pro Gly His Asn
                100                 105                 110

Tyr Thr Thr Arg Asn Ile Leu Pro Gly Leu Asn Ile Thr Cys Thr Phe
                115                 120                 125
```

His Lys Thr Gln Asn Pro Gln Cys Pro Ile Phe Arg Leu Gly Asp Ile
            130                 135                 140

Phe Arg Glu Thr Gly Asp Asn Phe Ser Asp Val Ala Ile Gln Gly Gly
145                 150                 155                 160

Ile Met Gly Ile Glu Ile Tyr Trp Asp Cys Asn Leu Asp Arg Trp Phe
                165                 170                 175

His His Cys Arg Pro Lys Tyr Ser Phe Arg Arg Leu Asp Asp Lys Thr
            180                 185                 190

Thr Asn Val Ser Leu Tyr Pro Gly Tyr Asn Phe Arg Tyr Ala Lys Tyr
        195                 200                 205

Tyr Lys Glu Asn Asn Val Glu Lys Arg Thr Leu Ile Lys Val Phe Gly
210                 215                 220

Ile Arg Phe Asp Ile Leu Val Phe Gly Thr Gly Gly Lys Phe Asp Ile
225                 230                 235                 240

Ile Gln Leu Val Val Tyr Ile Gly Ser Thr Leu Ser Tyr Phe Gly Leu
                245                 250                 255

Val Arg Asp Ser Leu Phe His Ala Leu Gly Lys Trp Phe Gly Glu Gly
            260                 265                 270

Ser Asp

<210> SEQ ID NO 10
<211> LENGTH: 258
<212> TYPE: PRT
<213> ORGANISM: Homo sapiens

<400> SEQUENCE: 10

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

```
-continued

Gln Cys Pro Ile Phe Arg Leu Gly Asp Ile Phe Arg Glu Thr Gly Asp
225                 230                 235                 240

Asn Phe Ser Asp Val Ala Ile Gln Ile Arg Gln Val Leu Gln Gly Lys
                245                 250                 255

Gln Cys

<210> SEQ ID NO 11
<211> LENGTH: 128
<212> TYPE: PRT
<213> ORGANISM: Homo sapiens

<400> SEQUENCE: 11

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
                20                  25                  30

Phe His Val Ile Ile Phe Ser Tyr Val Cys Phe Ala Leu Val Ser Asp
                35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
                100                 105                 110

Gly Gln Glu Gln Arg Leu Cys Pro Glu Glu Phe Arg Pro Glu Gly Val
            115                 120                 125

<210> SEQ ID NO 12
<211> LENGTH: 17
<212> TYPE: PRT
<213> ORGANISM: Homo sapiens

<400> SEQUENCE: 12

Gly His Asn Tyr Thr Thr Arg Asn Ile Leu Pro Gly Leu Asn Ile Thr
1               5                   10                  15

Cys
```